US010864325B2

(12) United States Patent
Cowe et al.

(10) Patent No.: US 10,864,325 B2
(45) Date of Patent: *Dec. 15, 2020

(54) AUTOMATIC INJECTION DEVICE

(71) Applicant: OWEN MUMFORD LIMITED, Oxfordshire (GB)

(72) Inventors: Toby Cowe, Oxford (GB); Colin Marc Webb, Cheshire (GB); Timothy Simon Evans, Oxfordshire (GB); Oliver Anderson, Oxfordshire (GB)

(73) Assignee: Owen Mumford Limited, Oxford (GB)

( * ) Notice: Subject to any disclaimer, the term of this patent is extended or adjusted under 35 U.S.C. 154(b) by 207 days.

This patent is subject to a terminal disclaimer.

(21) Appl. No.: 15/950,381

(22) Filed: Apr. 11, 2018

(65) Prior Publication Data
US 2018/0228974 A1    Aug. 16, 2018

Related U.S. Application Data

(63) Continuation of application No. 14/769,949, filed as application No. PCT/EP2014/053882 on Feb. 27, 2014, now Pat. No. 9,981,086.

(30) Foreign Application Priority Data

Feb. 27, 2013    (GB) .................................. 1303472.3

(51) Int. Cl.
*A61M 5/20* (2006.01)
*A61M 5/315* (2006.01)
(Continued)

(52) U.S. Cl.
CPC ...... *A61M 5/2033* (2013.01); *A61M 5/31571* (2013.01); *A61M 5/3204* (2013.01);
(Continued)

(58) Field of Classification Search
CPC .... A61M 2005/2073; A61M 2005/208; A61M 2005/2496; A61M 5/2033;
(Continued)

(56) References Cited

U.S. PATENT DOCUMENTS 9,421,336 B2 * 8/2016 Ekman .................. A61M 5/326
9,981,086 B2 * 5/2018 Cowe ................ A61M 5/31571
(Continued)

FOREIGN PATENT DOCUMENTS

EP        2675502        4/2010
EP    2 364 739 A1    9/2011
(Continued)

OTHER PUBLICATIONS

International Search Report, dated May 9, 2014, from corresponding PCT application.
(Continued)

*Primary Examiner* — Quynh-Nhu H. Vu
(74) *Attorney, Agent, or Firm* — Quarles & Brady LLP

(57) ABSTRACT

An automatic injection device for delivering a dose from a medicine containing syringe includes a housing for containing the syringe, a force applicator for applying a force to eject medicine from the syringe, a trigger coupled to the force applicator for releasing the force applicator to cause an injection, a boot covering a needle attached to the syringe to protect and maintain sterility of the needle, and a mechanical interlock. The mechanical interlock prevents actuation of the trigger prior to removal of the boot. When the boot is removed, the mechanical interlock allows for actuation of the trigger.

6 Claims, 35 Drawing Sheets

(51) Int. Cl.
*A61M 5/32* (2006.01)
*A61M 5/24* (2006.01)

(52) U.S. Cl.
CPC ............... *A61M 2005/208* (2013.01); *A61M 2005/2073* (2013.01); *A61M 2005/2496* (2013.01)

(58) Field of Classification Search
CPC ............ A61M 5/31571; A61M 5/3204; A61M 5/3202; A61M 2005/3217; A61M 2005/3247; A61M 2005/3267; A61M 2005/3238; A61M 2005/3264
See application file for complete search history.

(56) References Cited

U.S. PATENT DOCUMENTS

| | | | |
|---|---|---|---|
| 2003/0212370 A1* | 11/2003 | Barrelle | A61M 5/326 604/198 |
| 2010/0069846 A1* | 3/2010 | Stamp | A61M 5/2033 604/135 |
| 2010/0076379 A1* | 3/2010 | Matusch | A61M 5/30 604/135 |
| 2010/0256570 A1* | 10/2010 | Maritan | A61M 5/2033 604/198 |
| 2011/0118663 A1* | 5/2011 | Anderson | A61M 5/002 604/68 |
| 2012/0095408 A1 | 4/2012 | Eaton et al. | |
| 2012/0130342 A1 | 5/2012 | Cleathero | |
| 2012/0184917 A1 | 7/2012 | Bom | |
| 2012/0302989 A1* | 11/2012 | Kramer | A61M 5/30 604/500 |
| 2013/0190694 A1* | 7/2013 | Barrow-Williams | A61M 5/2033 604/198 |
| 2013/0274677 A1* | 10/2013 | Ekman | A61M 5/3202 604/197 |
| 2013/0289490 A1* | 10/2013 | Kemp | A61M 5/3287 604/198 |
| 2013/0296795 A1* | 11/2013 | Ekman | A61M 5/326 604/197 |
| 2013/0317446 A1* | 11/2013 | Hourmand | A61M 5/2033 604/196 |
| 2013/0324924 A1 | 12/2013 | Brereton | |
| 2014/0025006 A1* | 1/2014 | Takemoto | A61M 5/3245 604/110 |
| 2014/0336578 A1* | 11/2014 | Brereton | A61M 5/2033 604/135 |
| 2015/0343508 A1* | 12/2015 | Del Fabro | B21D 3/02 72/162 |

FOREIGN PATENT DOCUMENTS

| | | |
|---|---|---|
| GB | 2 414 398 A | 11/2005 |
| GB | 2 451 665 A | 2/2009 |
| GB | 2461078 | 12/2009 |
| GB | 2 467 637 A | 8/2010 |
| WO | 2005/070481 A1 | 8/2005 |
| WO | 2007036676 | 4/2007 |
| WO | 2009/040605 A1 | 4/2009 |
| WO | 2011/003979 A1 | 1/2011 |
| WO | 2012/045836 A2 | 4/2012 |

OTHER PUBLICATIONS

GB Search Report, dated Jul. 19, 2013, from corresponding GB application.
European Search Report 14707375.3 dated Jun. 30, 2016.

* cited by examiner

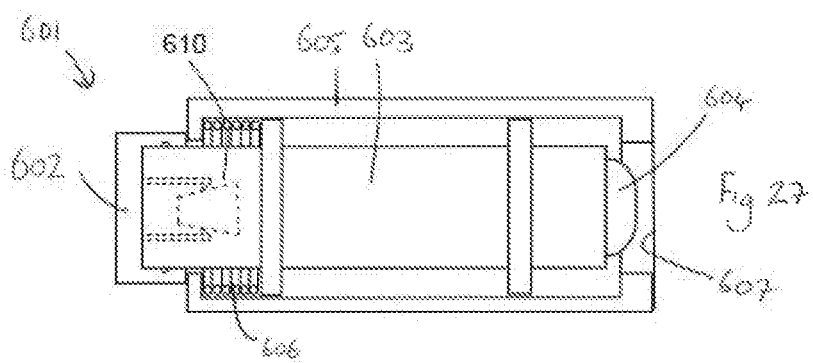
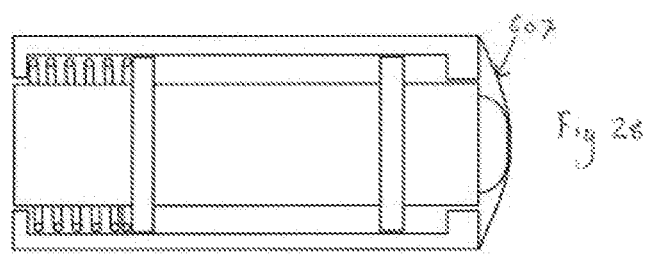
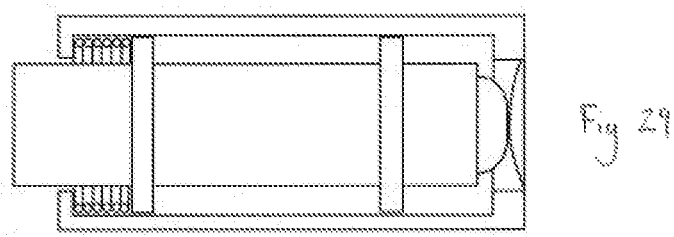
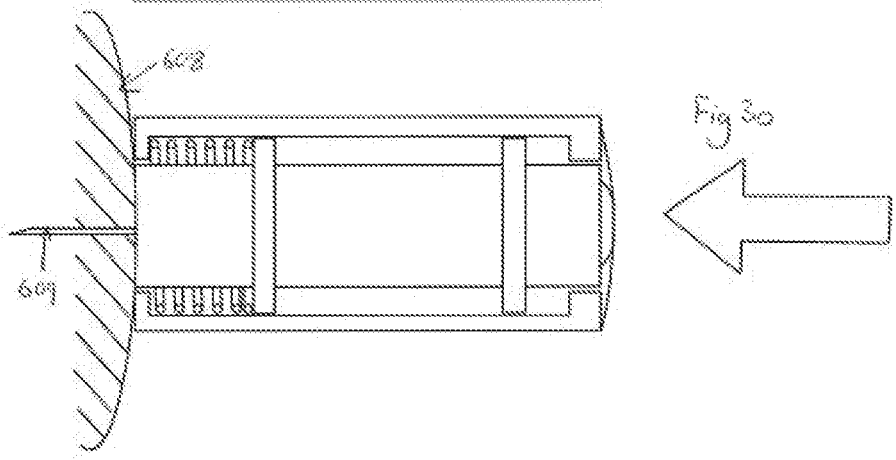

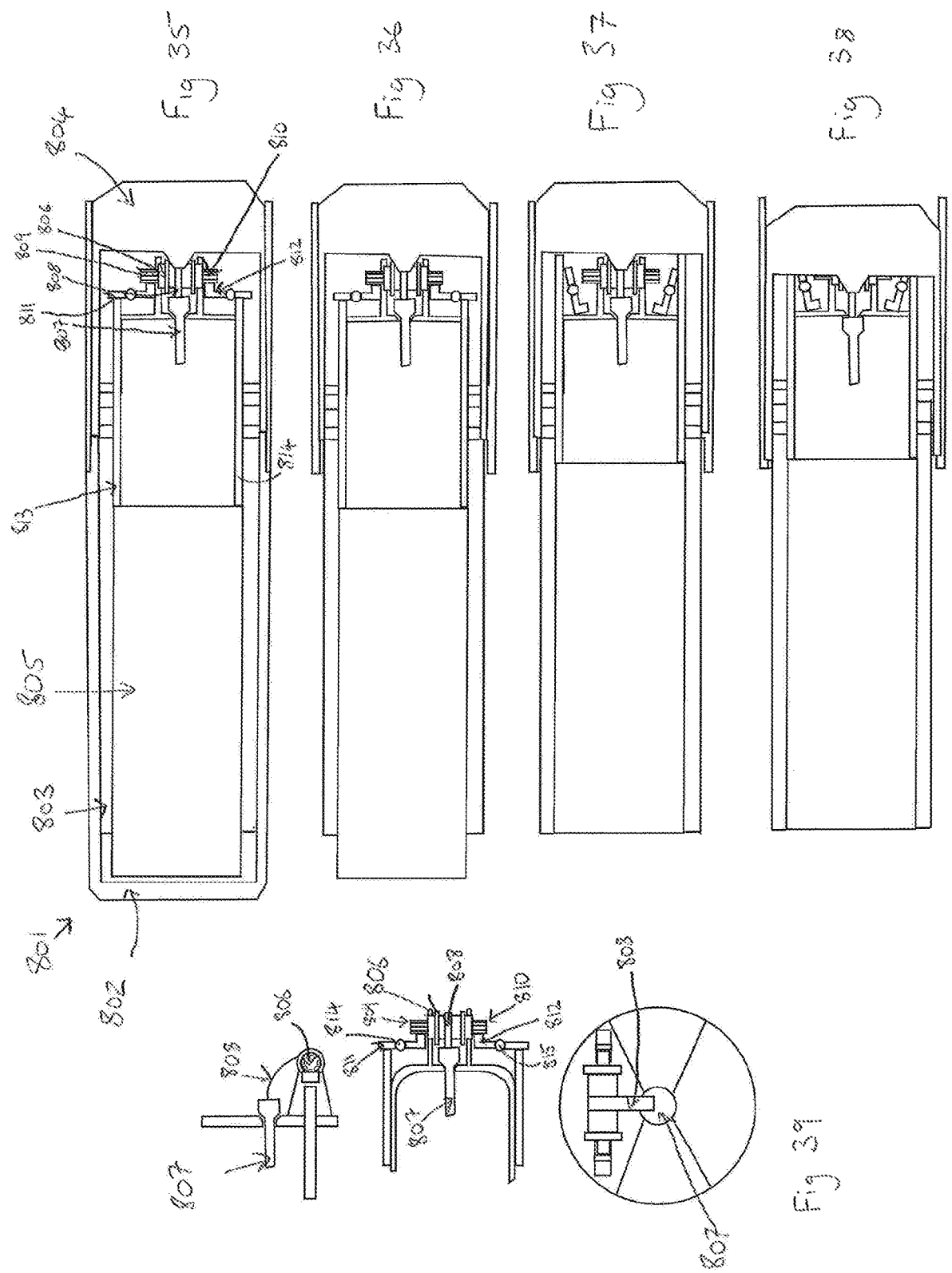

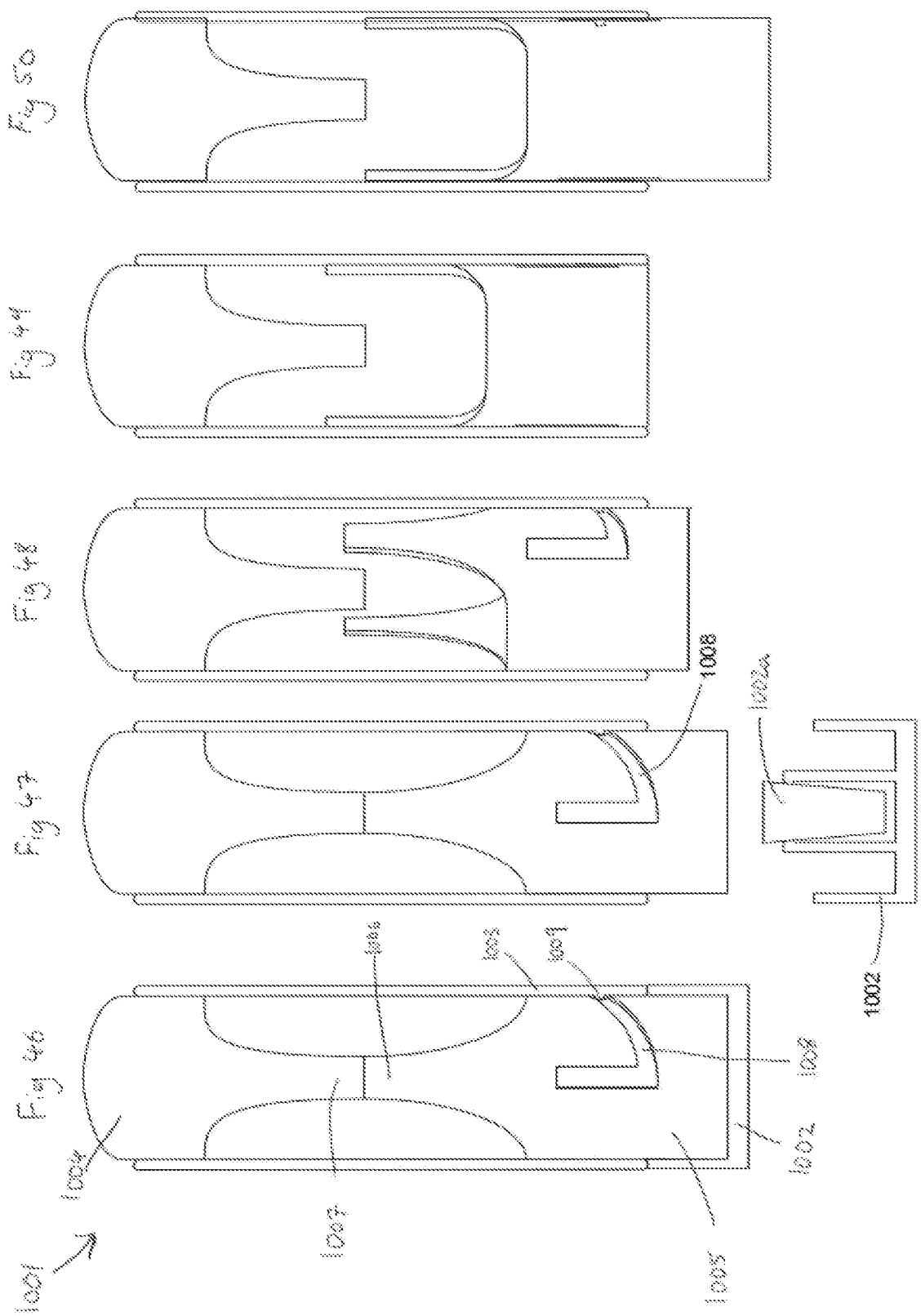

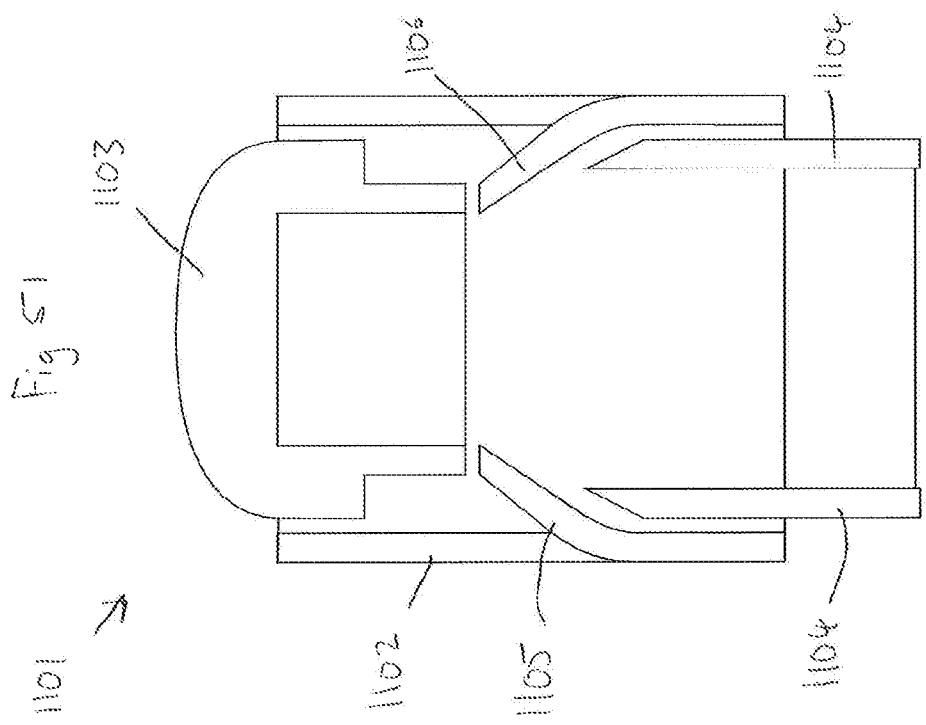
Fig S1, Fig S2, Fig S3

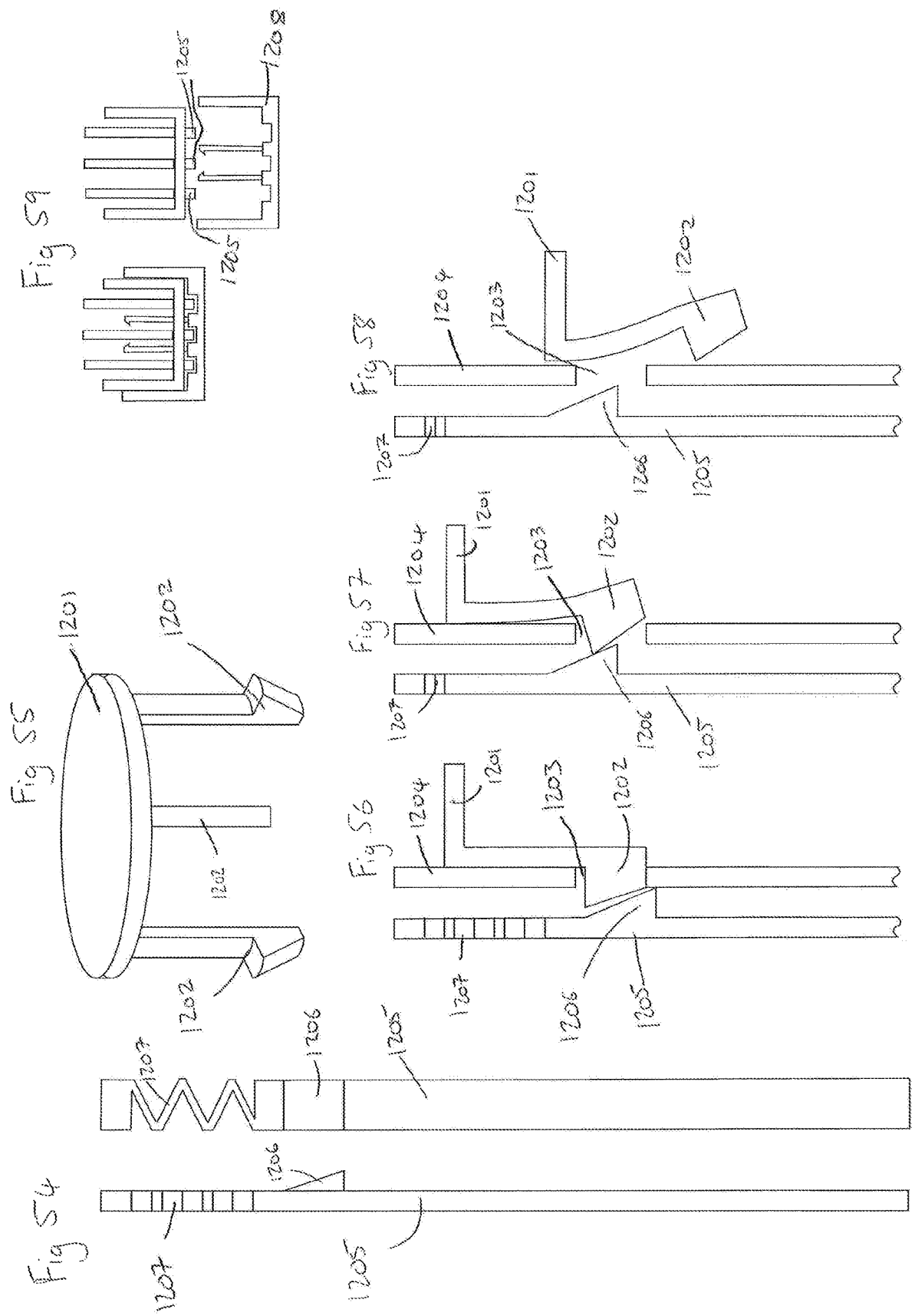

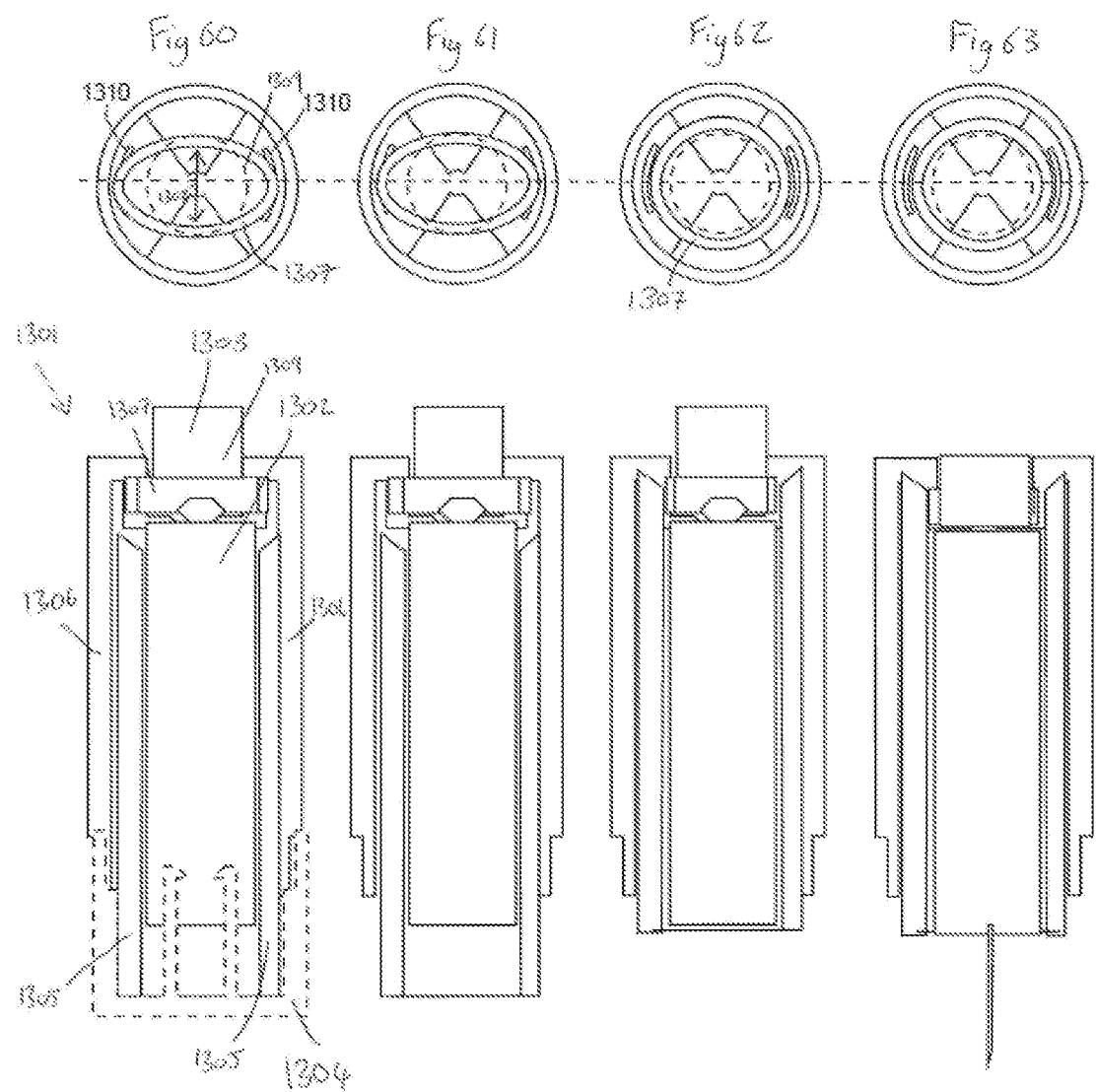

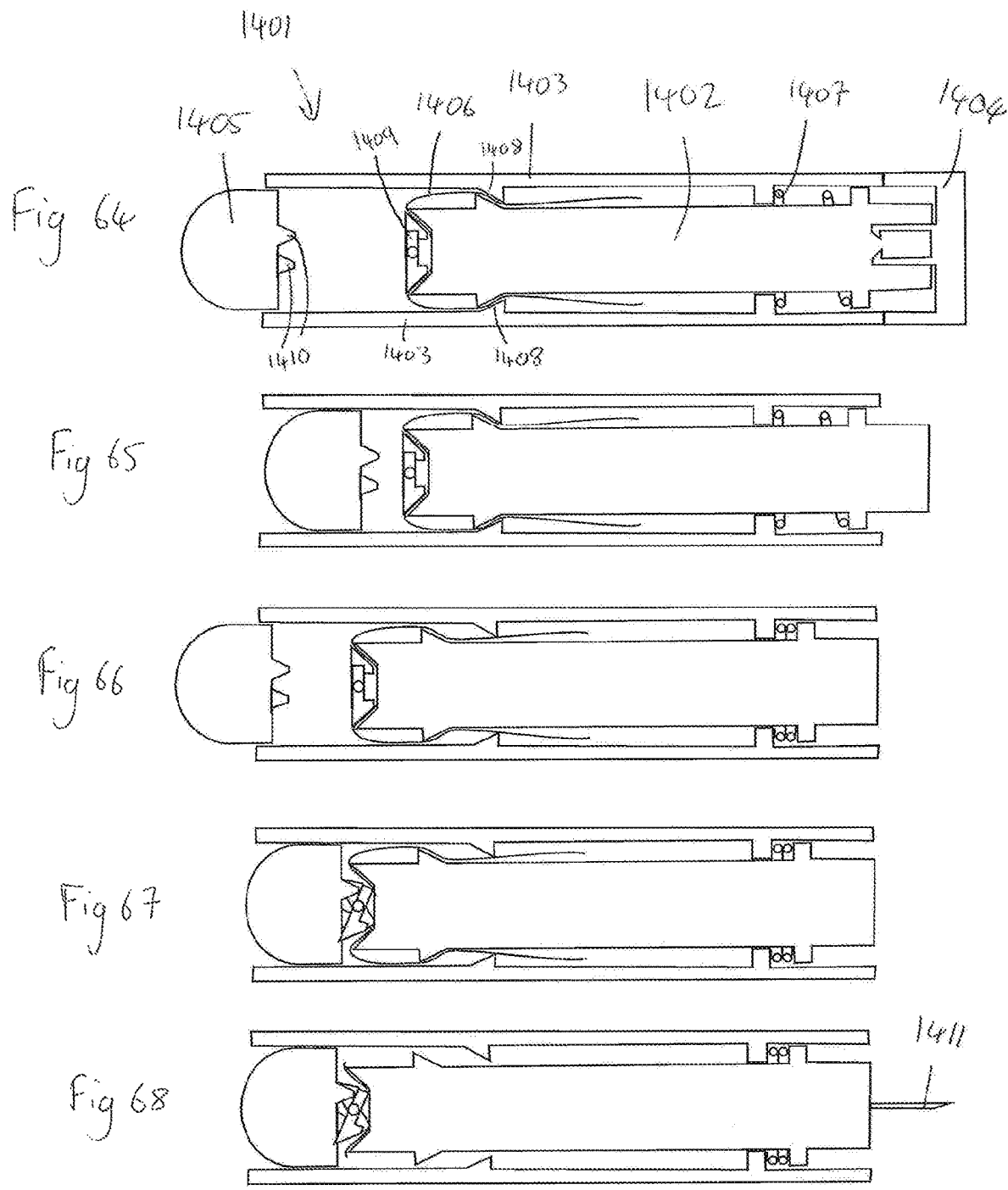

AUTOMATIC INJECTION DEVICE

TECHNICAL FIELD

The present invention relates to an automatic injection device for delivering a dose of medicine to a user from a medicine containing syringe.

BACKGROUND

Automatic injection devices are routinely used in the medical field to deliver a measured dose of medicine to a user. Due to their user friendly design, they can be safely used by patients for self-administration, although in some circumstances they may be used by trained personnel.

A typical automatic injection device comprises several parts which may include; a syringe containing medicine, a needle fixed to the end of the syringe, a firing mechanism including a spring (or possibly other drive means such as an electric motor or gas drive means), and a trigger. The spring may be preloaded, or may be set using a dose setting mechanism such as a dial. The firing mechanism is activated by the trigger and forces the medicine through the needle and into the user. A mechanical lock may be provided to prevent the trigger from being accidentally pressed. This could be, for example, simply a catch that must be moved out of the way in order to access the trigger.

Single use, disposable automatic injection devices are delivered to end users in an assembled state, with a medicine syringe contained within the device housing and a needle fixed to the end of the syringe. In order to ensure sterility of the needle, the projecting end of the needle is contained within an rubber or elastomer "boot". Typically, the boot forms an interference fit around the narrowed end portion of the syringe body. The tip of the needle may penetrate the end of the boot. In the case of re-useable automatic injection devices, an end user must typically open the housing and press a new single-use syringe into position. The single-use syringe will have a needle and boot already in place.

The injection device may also comprise a boot remover to allow the end user to easily and safely remove the boot and thereby expose the needle. Typically, the boot remover is fitted around or inside the proximal end of the device prior to insertion of the syringe into the housing. When the syringe is pressed into the housing, the boot protecting the needle is captured by the boot remover, i.e. snaps into place within the boot remover. A needle shield may be further provided around the needle, such that the needle remains protected even after the boot has been removed. This is relevant to so-called "auto-injectors" which, in addition to driving the medicine through the needle, perform an initial step of inserting the needle through the skin using the force provided by the injection spring (or possible a secondary spring).

When a single use automatic injection device is to be used, a user should first remove the boot remover and boot to expose the needle. NB. the needle remains surrounded by the needle shield at least in the case of an auto-injector. The user will then release the mechanical lock, such that the trigger can be pressed. The user can then place the auto-injector against the surface of the skin and press the trigger to push the needle through the skin and force the medicine through the needle. In the case of an auto-injector, a carriage and carriage-return spring may cause the needle to be returned to a position within the needle shield.

A problem with single use automatic injection devices occurs when a user forgets to first remove the boot, and, instead, operates the trigger with the boot still in place. This is particularly likely in the case of an auto-injector, where the needle and boot are not readily visible. If the boot is not removed before firing, no drug is delivered to the user. Furthermore, since the medicine will now be under pressure, there is a risk that the user may inadvertently empty the syringe contents into the air if, when realising their error, they subsequently remove the boot.

A user may not have an abundance of medicine and so waste may be a serious issue. Waste may also be undesirable due to cost implications: some medicines can be extremely expensive. Therefore, there exists a need to provide an automatic injection device that overcomes the problem of a device being fired prior to removal of a boot.

SUMMARY

It is an object of the present invention to provide an automatic injection device that cannot be fired prior to removal of a boot.

According to an aspect of the present invention there is provided an automatic injection device for delivering a dose from a medicine containing syringe. The automatic injection device comprises a housing for containing the syringe, a force applicator for applying a force to eject medicine from the syringe, a trigger coupled to the force applicator for releasing the force applicator to cause an injection, a boot covering a needle attached to the syringe to protect and maintain sterility of the needle, and a mechanical interlock. The mechanical interlock prevents actuation of the trigger prior to removal of the boot. When the boot is removed, the mechanical interlock allows for actuation of the trigger or commencement of an actuation sequence.

The present invention overcomes problems associated with current automatic injection devices, where a user can accidentally fire the automatic injection device with the boot still in place. This can result in wasted medicine, which may be expensive to replace. The present invention overcomes this by providing a mechanical interlock, such that an automatic injection device cannot be fired prior to removal of the boot.

As an option the automatic injection device comprises a boot remover for removing the boot. The boot remover may be formed integrally with the boot. Alternatively the boot and boot remover are formed as separate discrete components, and configured such that the boot is locked into the boot remover upon insertion of the syringe into the housing.

In a first embodiment of the present invention, the mechanical interlock comprises a boot remover, wherein the boot remover is configured such that removal of the boot remover from the housing both removes the boot from the needle and facilitates access to the trigger. As an option the mechanical interlock comprises a cover attached to a distal end of the housing. The cover is locked in place when the boot remover is attached to the housing, and is removable from the housing to expose the trigger only after removal of the boot remover and boot. As another option the cover is coupled to the distal end of the housing by one or more flexible latches. When the boot remover has been removed, the latches may be disengaged and the cover removed. The boot remover may extend to cover the flexible latches when the boot remover is attached to the housing.

In a second embodiment of the present invention, the housing comprises a first part for containing the syringe and a second part for attachment to the first part by a user. The mechanical interlock is configured to remove the boot upon coupling together of the first and second parts. As an option the trigger is provided on the second part. The first and second parts may be coupled together by relative axial motion of the parts, for example, by engaging complimentary screw threads formed on the first and second parts. The mechanical interlock may comprise a rod coupled to the first part of the housing and slideable relative thereto in an axial direction. The rod has a distal end that engages with the second part in order to axially displace the rod upon coupling together of the first and second parts. The rod has a proximal end that is coupled to the boot in order to remove the boot. As an option, the rod is coupled to the boot by way of the boot remover. As an option, the first part of the housing defines a channel within which the rod is slideably mounted. As an option the boot remover may comprise a peg that protrudes into the channel for engaging with the rod upon coupling together of the first and second parts in order to push the boot remover off of the housing. Alternatively, the housing comprises a spring coupled to the rod in order to return the proximal end of the rod into the channel upon disconnection of the first and second parts.

In a third embodiment of the present invention, the mechanical interlock comprises a rod coupled to the boot remover and a trigger lock engaging with the trigger and with said rod. The mechanical interlock is configured such that removal of the boot results in rotation of the rod thereby releasing the trigger lock. The rod may have a helical track extending axially therealong and a peg is provided on the boot remover to engage with said track such that the rotation of the rod is caused by the axial motion of the peg as the boot remover is removed. As an option the boot remover may comprise a key and the housing may comprise an axially extending track. The key and axially extending track are arranged such that the key engages with the axially extending track to prevent rotation of the boot remover prior to removal of the boot remover.

In a fourth embodiment of the present invention, the mechanical interlock comprises a rod coupled to the boot remover and a trigger lock engaging with the trigger and with said rod. The mechanical interlock is configured such that removal of the boot results in rotation of the rod thereby releasing the trigger lock. A torsion spring is coupled between the rod and the hosing to provide a rotational bias to the rod. A latch is provided on the boot remover to prevent rotation of the rod until the boot remover has been removed. As an option the rod comprises a pin for engaging with the latch. As an option the boot remover may comprise a key and the housing may comprise an axially extending track. The key and axially extending track are arranged such that the key engages with the axially extending track to prevent rotation of the boot remover prior to removal of the boot remover.

In a fifth embodiment of the present invention, the housing comprises a first part for containing the syringe and a second part for attachment to the first part by the user. The mechanical interlock is provided by the boot remover such that, when attached to the first and second parts, the boot remover holds the first and second parts in a non-useable configuration and removal of the boot remover allows the first and second parts to be brought together into a useable configuration. As an option, there is provided a hinge that rotatably couples the first and second parts together. The mechanical interlock may further comprise a trigger lock for preventing actuation of the trigger when the device is in the non-useable configuration whilst allowing actuation of the trigger when the device is in the useable configuration. The trigger lock may comprise an elongate plate mounted to the first part by a pivot axle. There may be a biasing mechanism acting on the plate such that, when in the non-usable configuration, the plate prevents actuation of the trigger. When the device is brought together into a useable configuration, the plate is rotated about said axle to free the trigger.

Further aspects of the present invention are set out in the accompanying claims.

BRIEF DESCRIPTION OF DRAWINGS

FIG. 27 shows a cross-section view of an auto-injector according to a sixth embodiment;

FIG. 28 shows a cross-section view of the auto-injector of FIG. 27 with a boot remover removed;

FIG. 29 shows a cross-section view of the auto-injector of FIG. 27 when the trigger is pressed and the device is not pressed against the skin;

FIG. 30 shows a cross-section view of the auto-injector of FIG. 27 being activated;

FIG. 35 shows a cross-section view of an auto-injector according to an eighth embodiment;

FIG. 36 shows a cross-section view of the auto-injector of FIG. 35 following removal of a boot remover;

FIG. 37 shows a cross-section view of the auto-injector of FIG. 35 when pressed against the skin;

FIG. 38 shows a cross-section view of the auto-injector of FIG. 35 with the trigger depressed;

FIG. 39 shows alternative views of a locking mechanism;

FIG. 46 shows a cross-section view of an auto-injector according to a tenth embodiment;

FIG. 47 shows a cross-section view of the auto-injector of FIG. 46 with the boot remover removed;

FIG. 48 shows a cross-section view of the auto-injector of FIG. 46 when pressed against the skin;

FIG. 49 shows a further cross-section view of the auto-injector of FIG. 46 when pressed against the skin;

FIG. 50 shows a further cross-section view of the auto-injector of FIG. 46;

FIG. 51 shows a cross-section view of a locking mechanism according to an eleventh embodiment;

FIG. 52 shows a cross-section view of the locking mechanism after disengagement;

FIG. 53 shows a cross-section view of the locking mechanism with the trigger depressed;

FIG. 54 shows a perspective view of a release element according to a twelve embodiment of the present invention;

FIG. 55 shows a perspective view of a trigger according to a twelfth embodiment of the present invention;

FIG. 56 shows a cross section of the twelfth embodiment;

FIG. 57 shows a cross section of the twelfth embodiment;

FIG. 58 shows a cross section of the twelfth embodiment;

FIG. 59 shows a boot remover of the twelfth embodiment;

FIG. 60 shows a top cross sectional view and side view of an auto-injector according to thirteenth embodiment of the present invention;

FIG. 61 shows a top cross sectional view and side view of the auto-injector of FIG. 60 with the boot remover remvoed;

FIG. 62 shows a top cross sectional view and side view of the auto-injector of FIG. 60 when pressed against the skin;

FIG. 63 shows a top cross sectional view and side view of the auto-injector of FIG. 60 when activated;

FIG. 64 shows a cross sectional view of an auto-injector according to fourteenth embodiment of the present invention;

FIG. 65 shows a cross sectional view of the auto-injector of FIG. 64 with the boot remover removed and the button depressed;

FIG. 66 shows a cross sectional view of the auto-injector of FIG. 64 when pressed against the skin;

FIG. 67 shows a cross sectional view of the auto-injector of FIG. 64 when the button is depressed and the device is pressed against the skin; and FIG. 68 shows a cross sectional view of the auto-injector of FIG. 64 once activated.

DETAILED DESCRIPTION

Embodiments to be described aim to provide an automatic injection device that cannot be fired until a boot protecting the syringe needle has been removed. The aim is to prevent the problem of wasted medicine and user frustration that may otherwise occur. Embodiments are described in the context of an auto-injector, that is an automatic injection device that has a spring or springs that not only drives the injection of medicine, but also pushes the needle into the patient's skin. Such a device is referred to as an auto-injector. However, the skilled person will appreciate that the approach may also be applied to automatic injection devices that only drive medicine delivery and do not push the needle into the skin.

Figure 1:
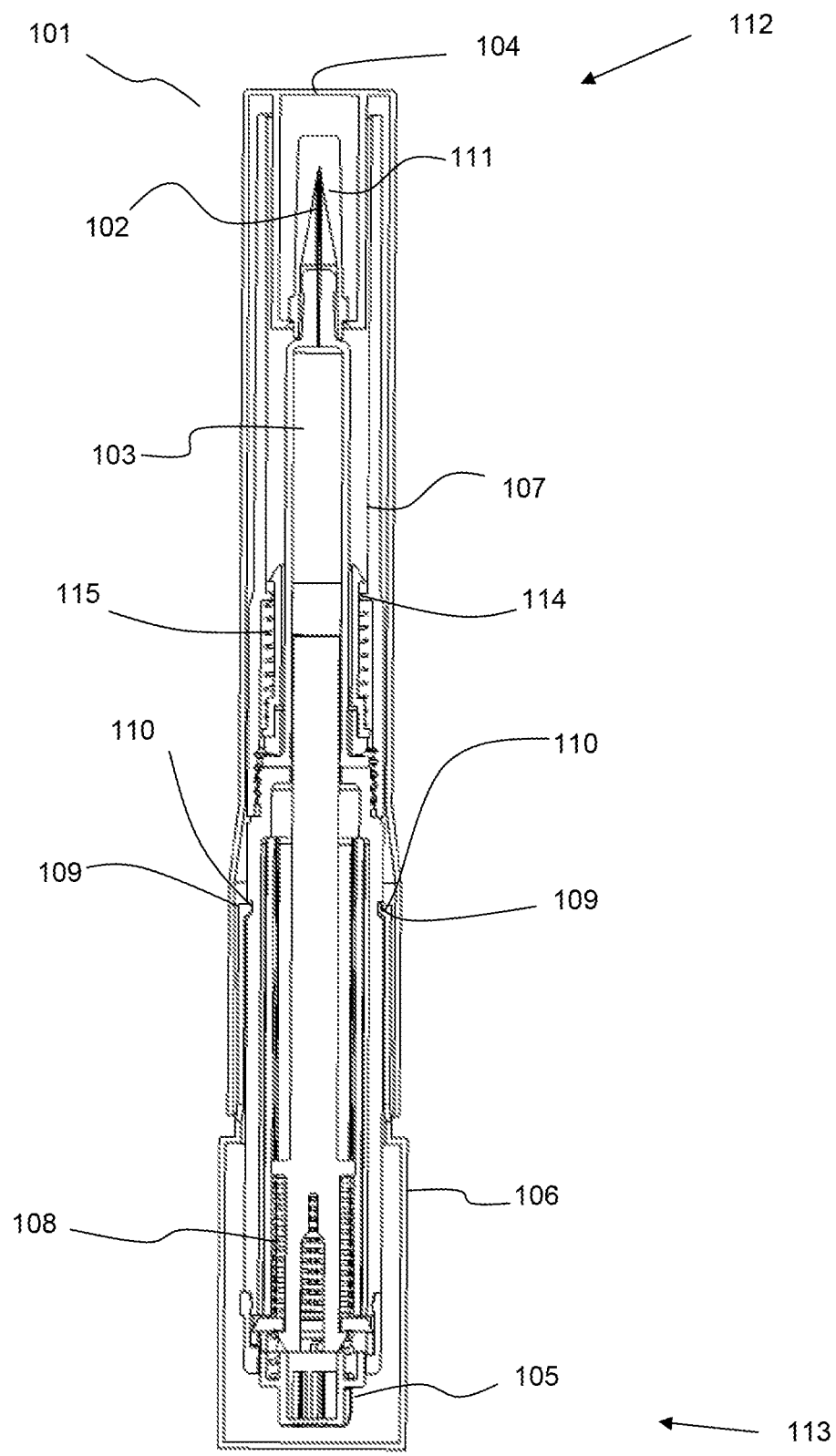
FIG. 1 shows a cross-section through an auto-injector according to a first embodiment.
Figure 2:
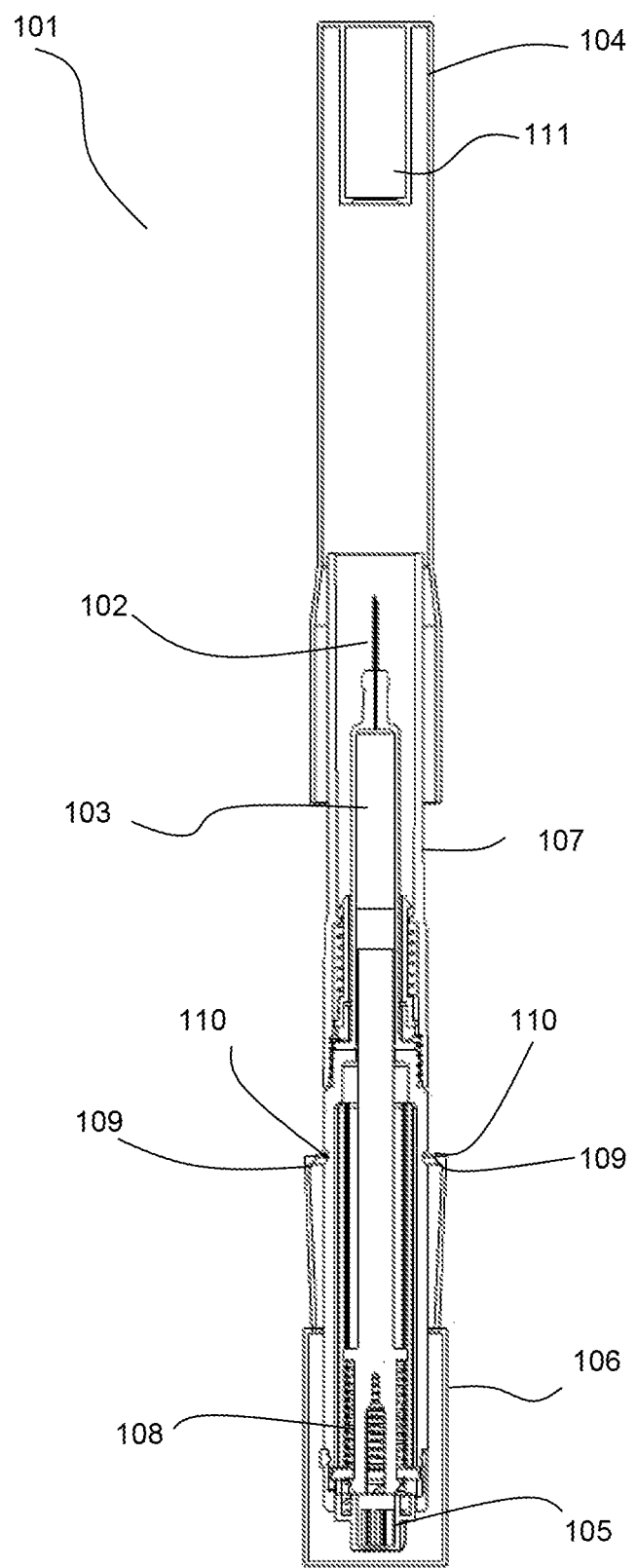
FIG. 2 shows a cross-section through the auto-injector of FIG. 1 with a boot remover partially removed.
Figure 3:
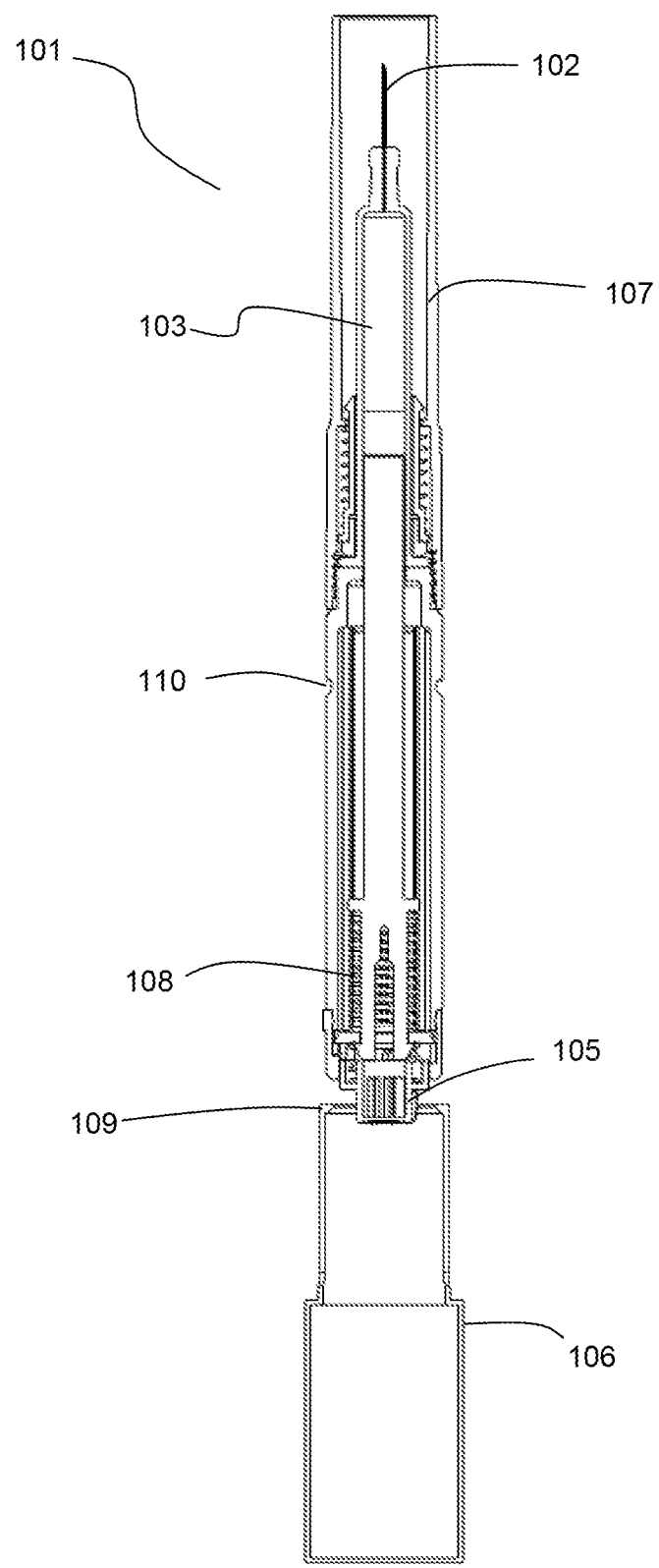
FIG. 3 shows a cross-section through the auto-injector of FIG. 1 with a trigger cover partially removed.

With reference to FIGS. 1 to 3, there will now be described a first embodiment, referred to here as the "enclosed button auto-injector". To assist with an understanding of this and further embodiments described below it is helpful to define a "proximal" end of the auto-injector as being the end that is closest to the patient's skin when in use, and a "distal" end as being the end furthest from the patient's skin.

FIG. 1 shows a cross-sectional view of an enclosed button auto-injector 101 comprising a needle 102, syringe 103, boot remover 104, boot 111, trigger 105, trigger cover 106, and housing 107. The auto-injector has a proximal end 112 and a distal end 113. The housing 107 houses the needle 102 for piercing a user's skin, and the syringe 103 for containing medicine. Activation of the trigger 105 actuates a firing mechanism 108. The firing mechanism 108 drives the needle into the skin, and forces the medicine through the needle and into the user. Although not described in detail, the device also includes a carriage 114 and carriage return spring 115 within which the syringe 103 is mounted.

To prevent the user from accidentally activating the trigger 105, the trigger cover 106 is removably attached to the housing 107 such that it covers the trigger 105. This provides a physical barrier that prevents the user from accidentally activating the trigger 105. Any suitable mechanical interlock for preventing activation of the trigger 105, such as a trigger lock, may be used instead of the trigger cover 106. When the user wishes to use the enclosed button auto-injector 101, he or she must first remove the trigger cover 106 in order to access the trigger 105.

The trigger cover 106 may be secured to the housing 107 by any suitable connection type. For example, in FIGS. 1 and 2 the trigger cover 106 has ridges 109 for slotting into shoulders 110 formed in the housing 107.

The boot 111 is arranged to prevent contamination of the needle 102. The boot remover 104 is connected to the boot, and facilitates removal of the boot. The boot remover 104 extends over the outer surface of the housing 107 and over the ridges 109 of the trigger cover 106. By doing so, the boot remover 104 prevents any lateral displacement of ridges 109, and therefore prevents the ridges 109 from being moved out of the shoulders 110, preventing removal of the trigger cover 106. The boot remover 104 may provide support to the ridges 109, holding them in place within the shoulders 110.

FIG. 2 shows the boot remover 104 partially removed from the housing 107, no longer preventing the ridges 109 from lateral movement. The ridges 109 are pre-stressed and splay outwardly upon removal of the boot remover 104 to disengage from the shoulders 110. In an alternative configuration, the ridges may by displaced outwardly by a separate biasing mechanism, e.g. a spring. FIG. 3 shows the boot remover 104 totally removed from the device 101, and the trigger cover 106 partially removed. As a result, the trigger 105 is now exposed.

This arrangement forces a user to perform the step of removing the boot 111 using the boot remover 104 before pressing the trigger 105. By doing so, accidentally activating the enclosed button auto-injector 101 while the boot 111 is still in place is not possible.

This example is but one of many ways in which the boot remover 104 can prevent removal of the trigger cover 106. For example, the boot remover 104 may act as an interlock to a button, where the button may be used to facilitate removal of the trigger cover 106.

With reference to FIGS. 4 to 7, there will now be described a second embodiment, referred to here as the "embedded rod auto-injector".

Figure 4:
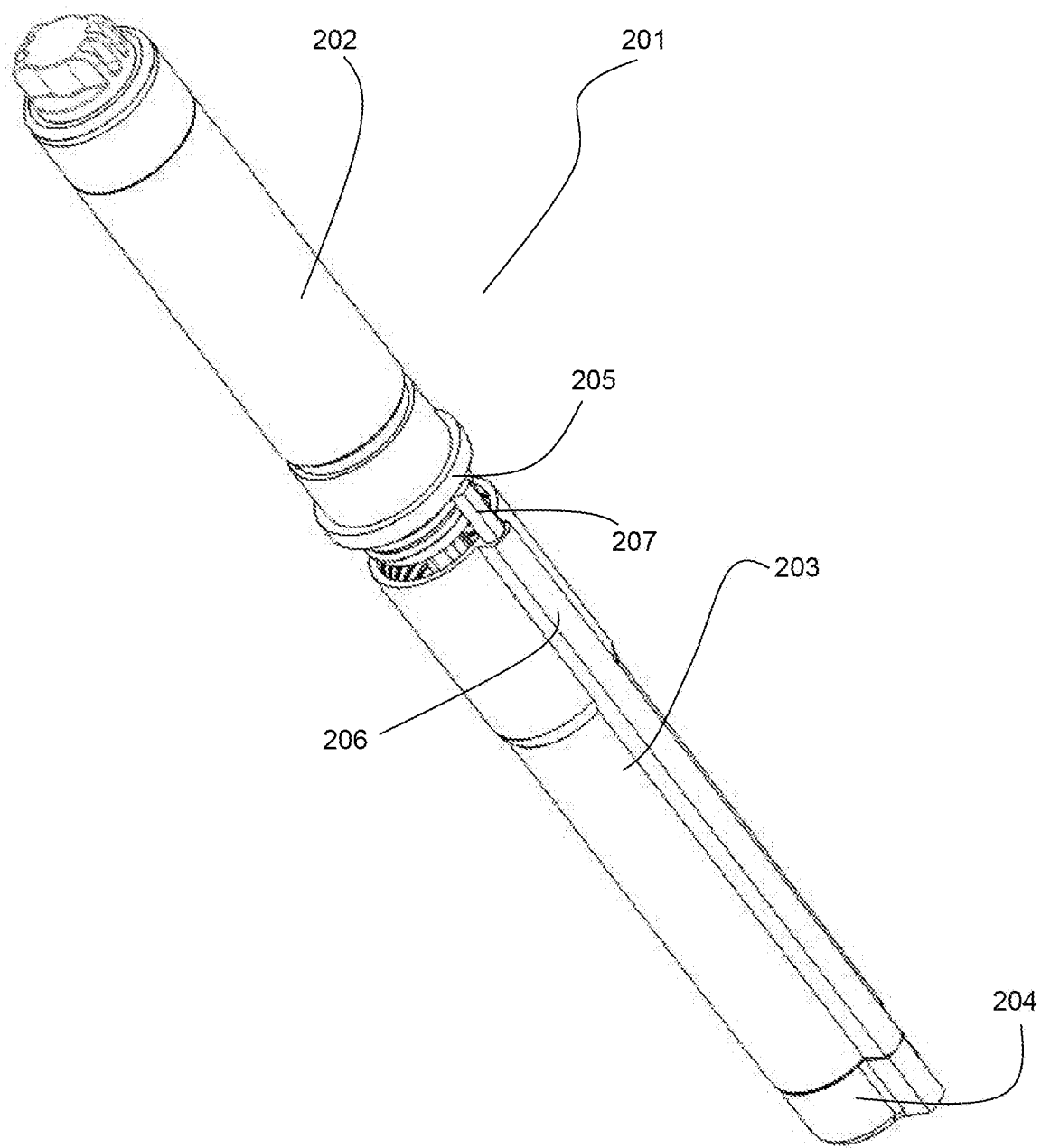
FIG. 4 shows a perspective view of an auto-injector according to a second embodiment.

FIG. 4 illustrates an embedded pin or rod auto-injector 201, comprising a firing mechanism housing 202, a syringe housing 203 containing a syringe, needle and boot (not shown), and a boot remover 204. Initially, the firing mechanism housing 202 is separate from the syringe housing 203, and therefore actuation of the firing mechanism within the firing mechanism housing 202 will not actuate the injection. On assembly of the embedded rod auto-injector 201, a lip 205 on the firing mechanism housing 202 displaces a rod 207 residing in a channel 206 in the syringe housing 203. Assembly may be achieved by screwing the firing mechanism housing 202 into the syringe housing 203.

Figure 5:
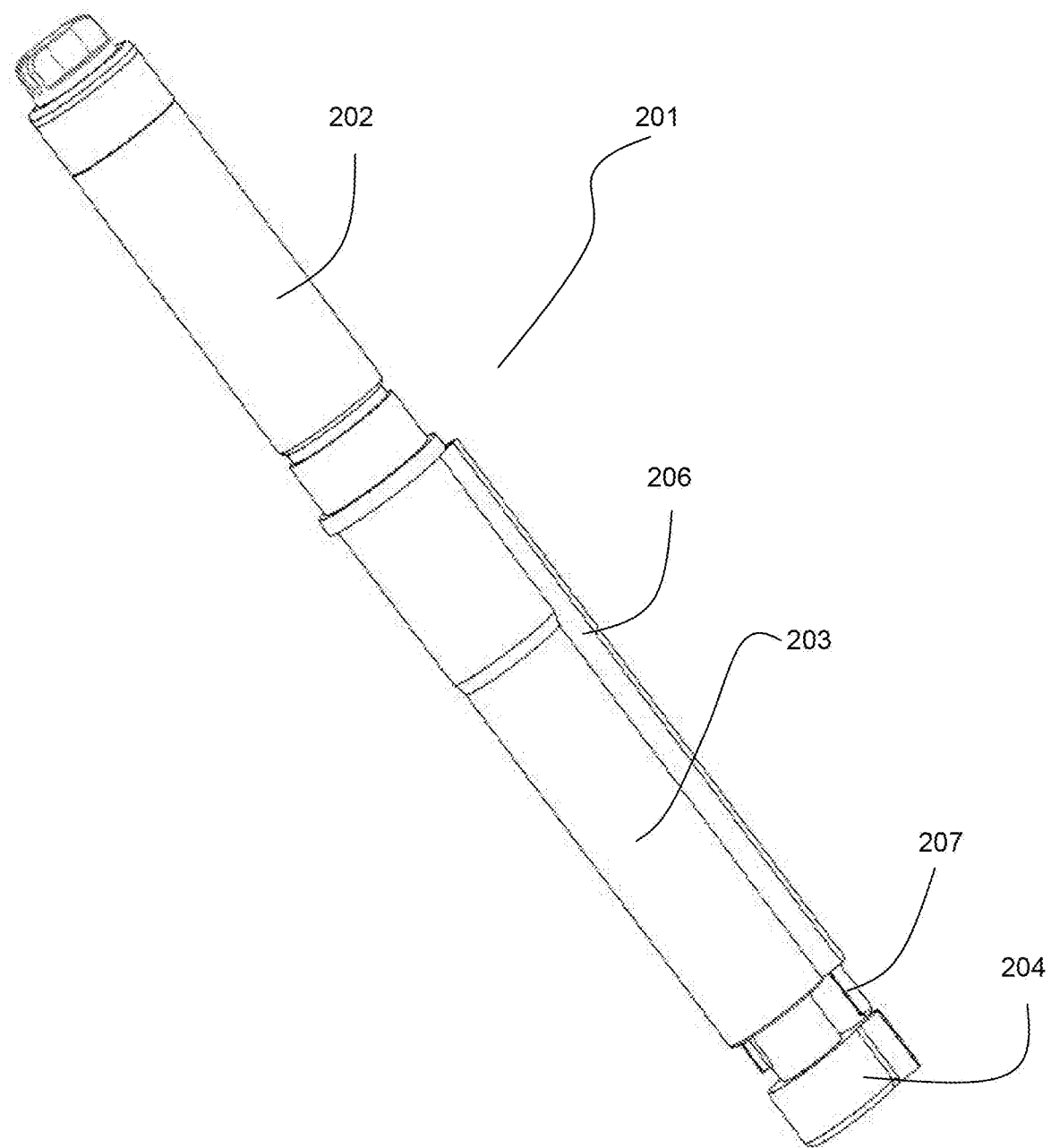
FIG. 5 shows a perspective view of the auto-injector of FIG. 4 with a boot remover partially removed.
Figure 6:
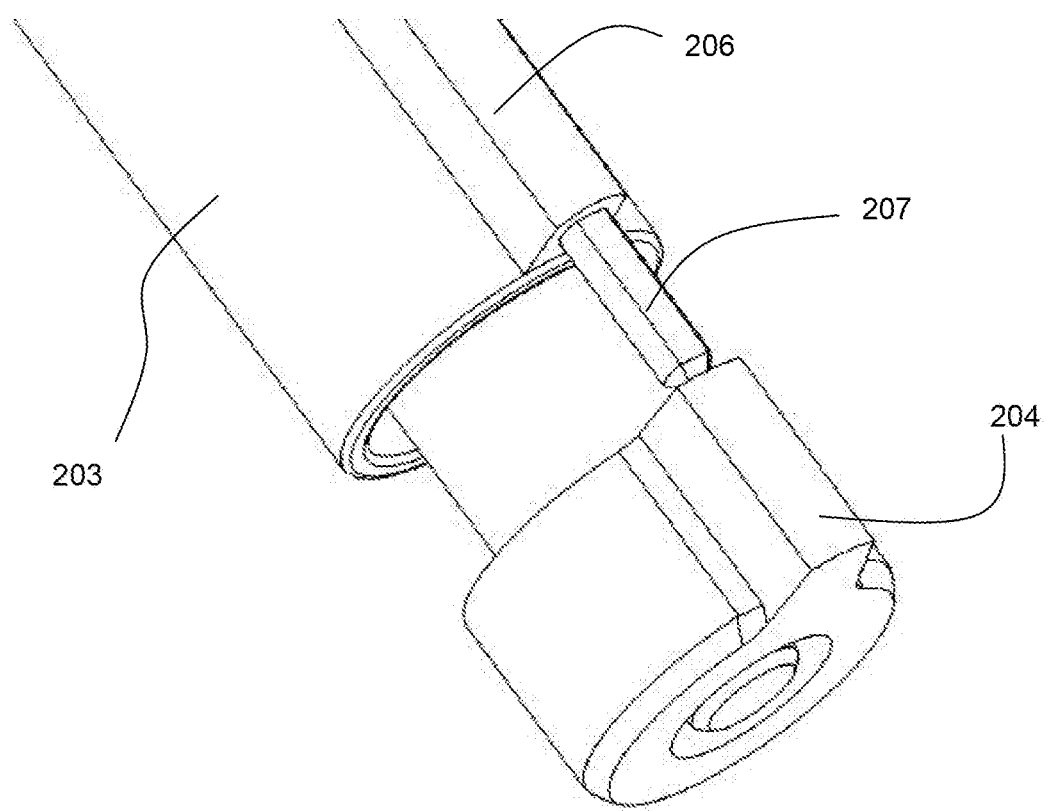
FIG. 6 shows a close up perspective view of a proximal end of the auto-injector of FIG. 4.

FIG. 5 shows the firing mechanism housing 202 fully engaged with the syringe housing 203. The lip 205 has displaced the rod 207, which has in turn displaced the boot remover 204, removing it from the syringe housing 203. As a result, the boot will be removed before the auto-injector 201 can be actuated. FIG. 6 shows a close up view of the rod 207 displacing the boot remover 204.

Figure 7:
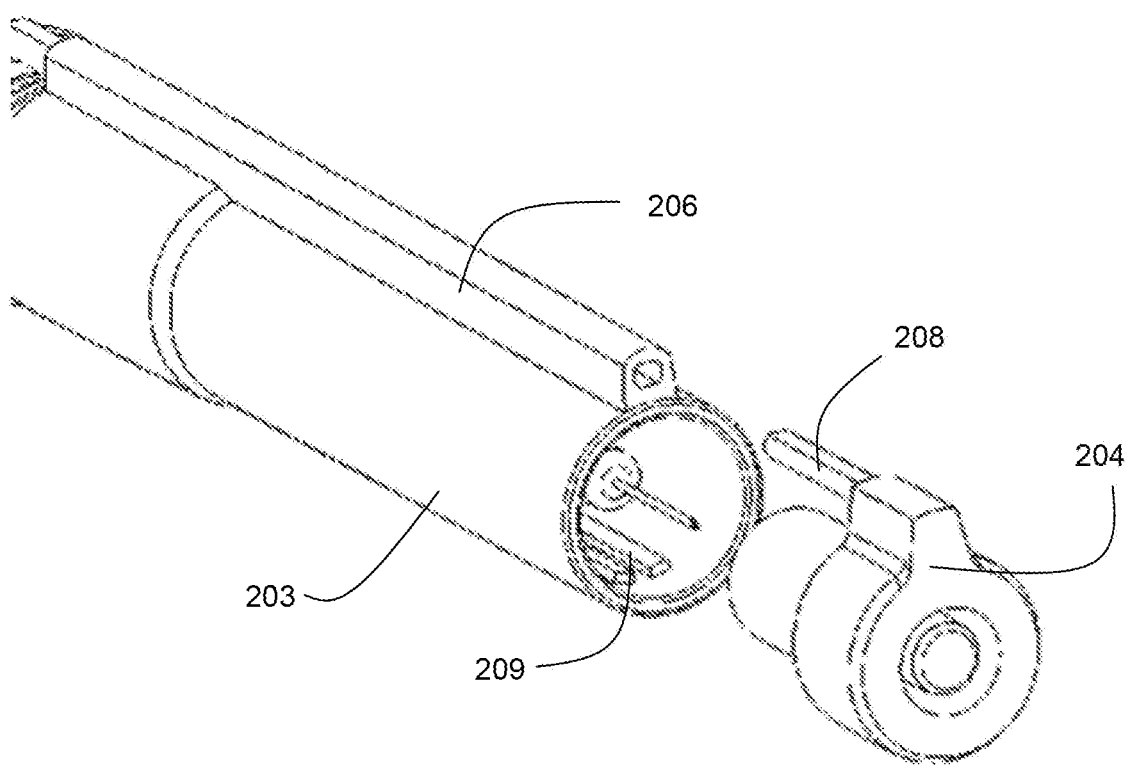
FIG. 7 shows a further close up perspective view of a proximal end of the auto-injector of FIG. 4 with boot remover removed.

The boot remover 204 may have a peg 208 that protrudes into the channel 206 for engaging with the rod, shown in FIG. 7. This arrangement ensures that the boot remover 204 can be displaced and ejected without subsequent protrusion of the rod 207, which may otherwise lead to an obstruction when administering an injection. FIG. 7 also shows a track 209 running along the inner surface of the syringe housing 203, for receiving a ridge (not shown) formed on the boot remover 204, ensuring proper alignment of the boot remover 204.

The embedded rod auto-injector 201 may comprise a spring located within the syringe housing 203 that acts to push the rod 207 backwards (toward firing mechanism housing 202) in order to ensure that the rod 207 returns from the protruding position upon disassembly. This is relevant in particular to a re-useable device.

With reference to FIGS. 8 to 13, there will now be described a third embodiment, referred to here as the "helical linkage auto-injector".

Figure 8:
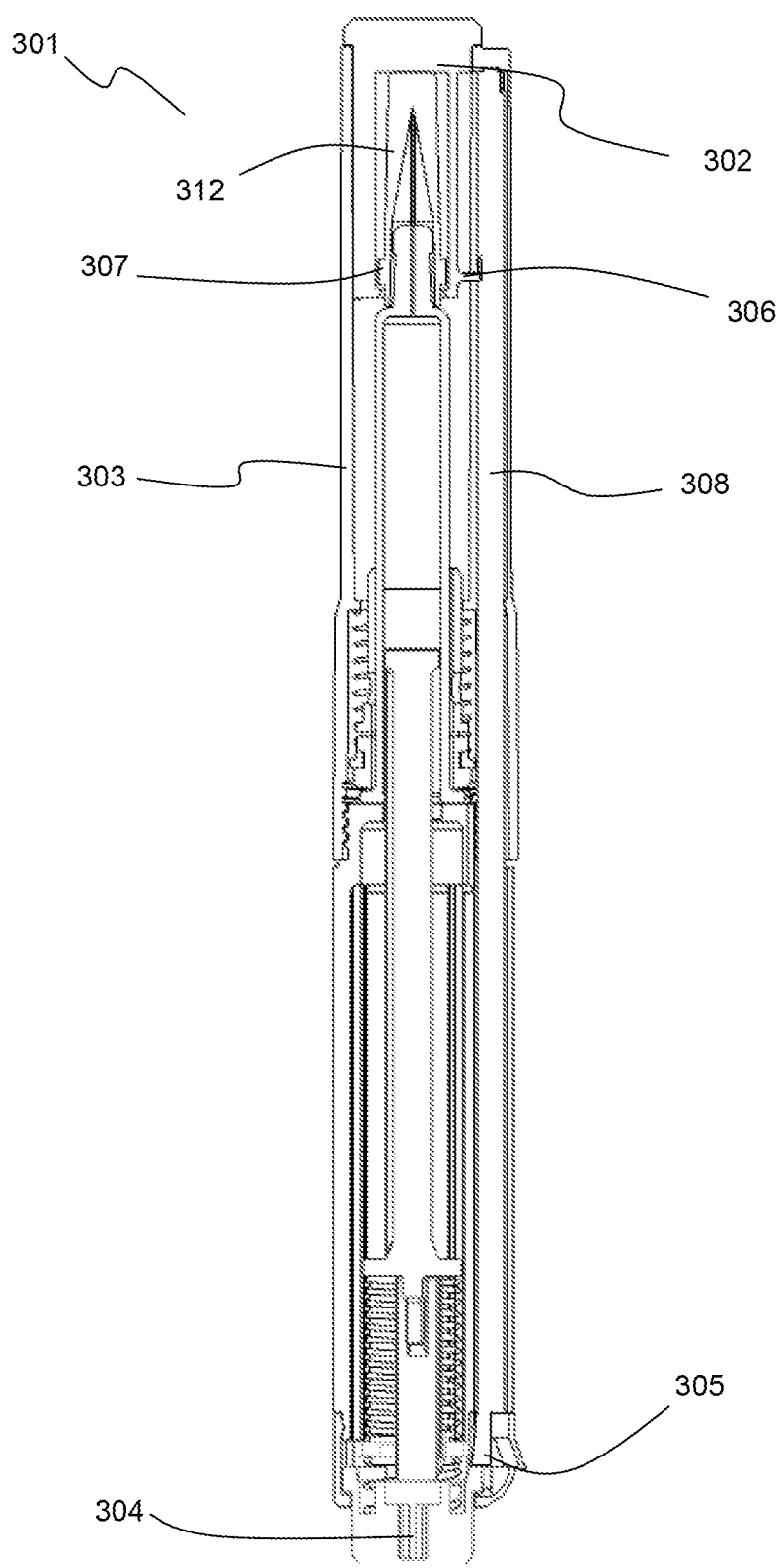
FIG. 8 shows a cross-section through an auto-injector according to a third embodiment.

FIG. 8 shows a cross-section of a helical linkage auto-injector 301, comprising a boot remover 302, boot 312, housing 303, trigger 304 and trigger lock 305.

The boot remover 302 has a radially projecting peg 306 and a key 307. The housing 303 has an axial track (not shown) for receiving the key 307, and is arranged to prevent rotation of the boot remover 302 while the key 307 is engaged with the axial track. Any number of ways can be used to prevent rotation of the boot remover 302 while it is attached to the helical linkage auto-injector 301. The use of a key 307 and axial track is just one of many possible alternatives.

Figure 9:
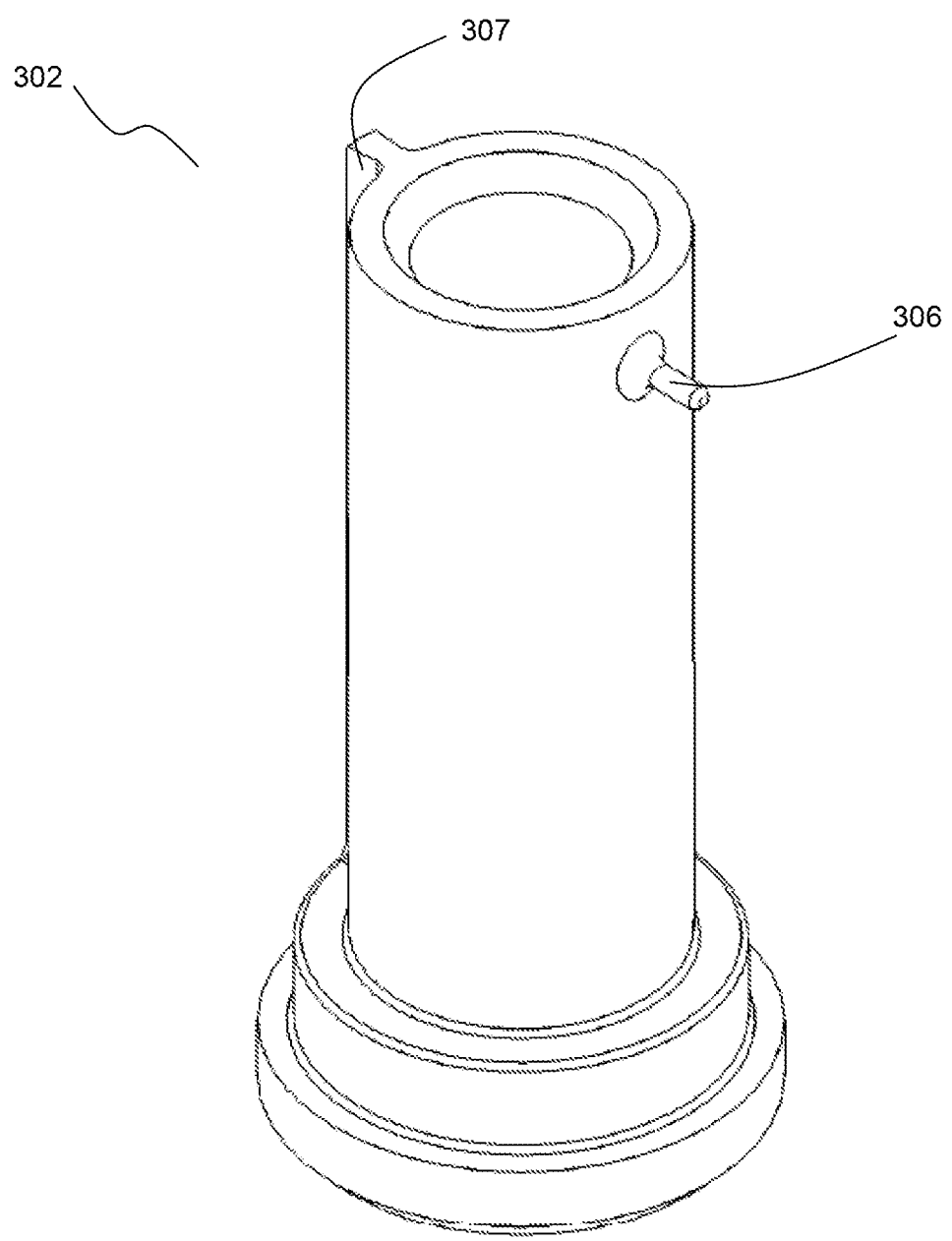
FIG. 9 shows a perspective view of a boot remover according to an option of the third embodiment.
Figure 10:
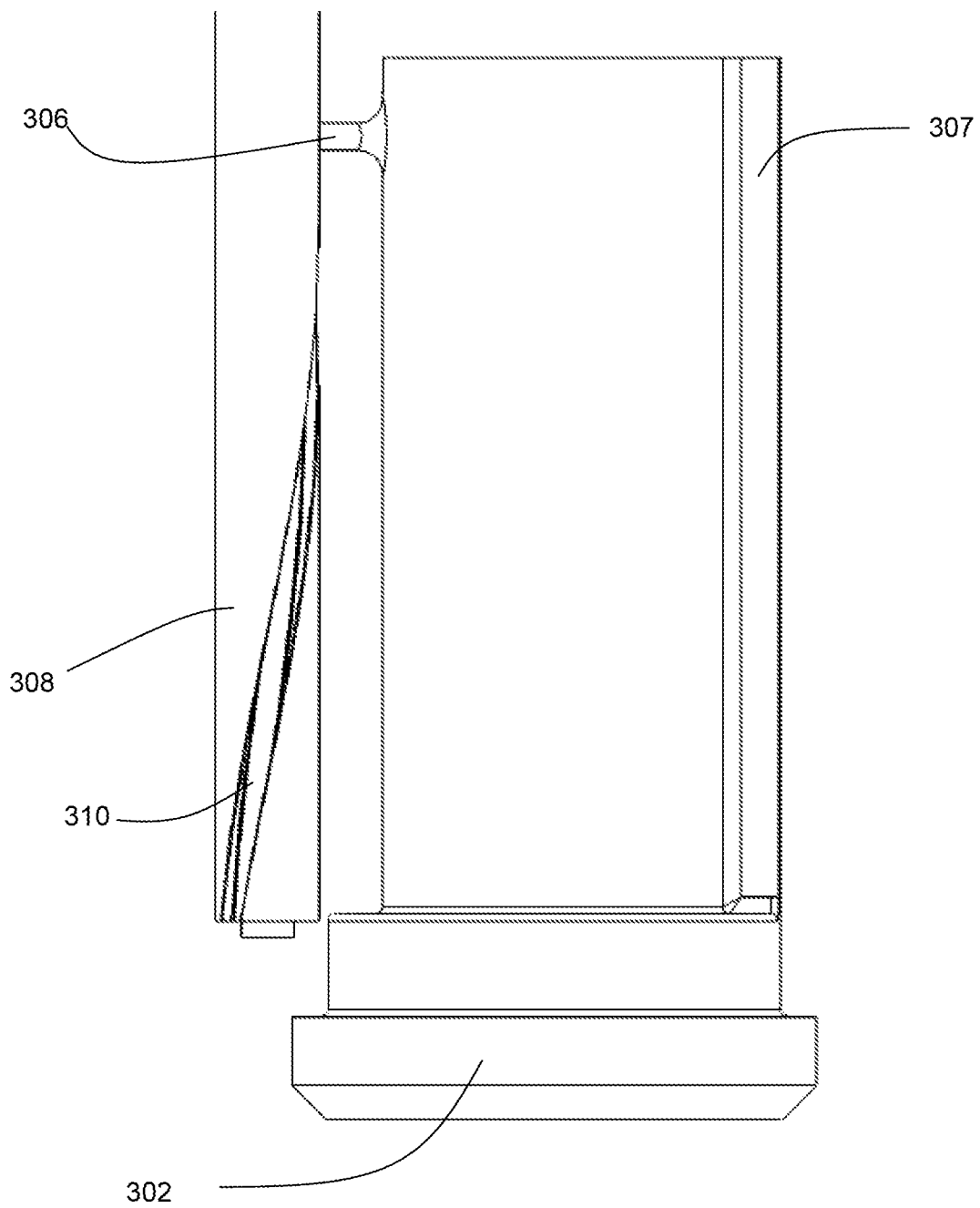
FIG. 10 shows a side view of the boot remover of the third embodiment engaging with a rod.

The housing 303 contains a rod 308 with a helical track 310 (not shown in FIG. 8) running around its circumference. The helical track 310 is arranged to receive the peg 306. Note that when the peg 306 is engaged with the helical track 310, the connection between the peg 306 and helical track 310 may be sufficient to prevent rotational movement of the boot remover 302. The key 307 and axial track may then not be required. At one end of the rod 308 there is a trigger lock 305 for preventing actuation of the trigger 304. The trigger lock 305 features is shaped such that, in one orientation of the rod 308 and trigger lock 305, the trigger 304 cannot be activated, but, when the rod and trigger lock are rotated 180 degrees, the trigger 304 can be activated. The shape may be a stepped shape for example. FIG. 9 shows a perspective view of the boot remover 302, showing the peg 306 and a key 307, whilst FIG. 10 shows the peg 306 engaging with the helical track 310 on the rod 308.

Figure 11:
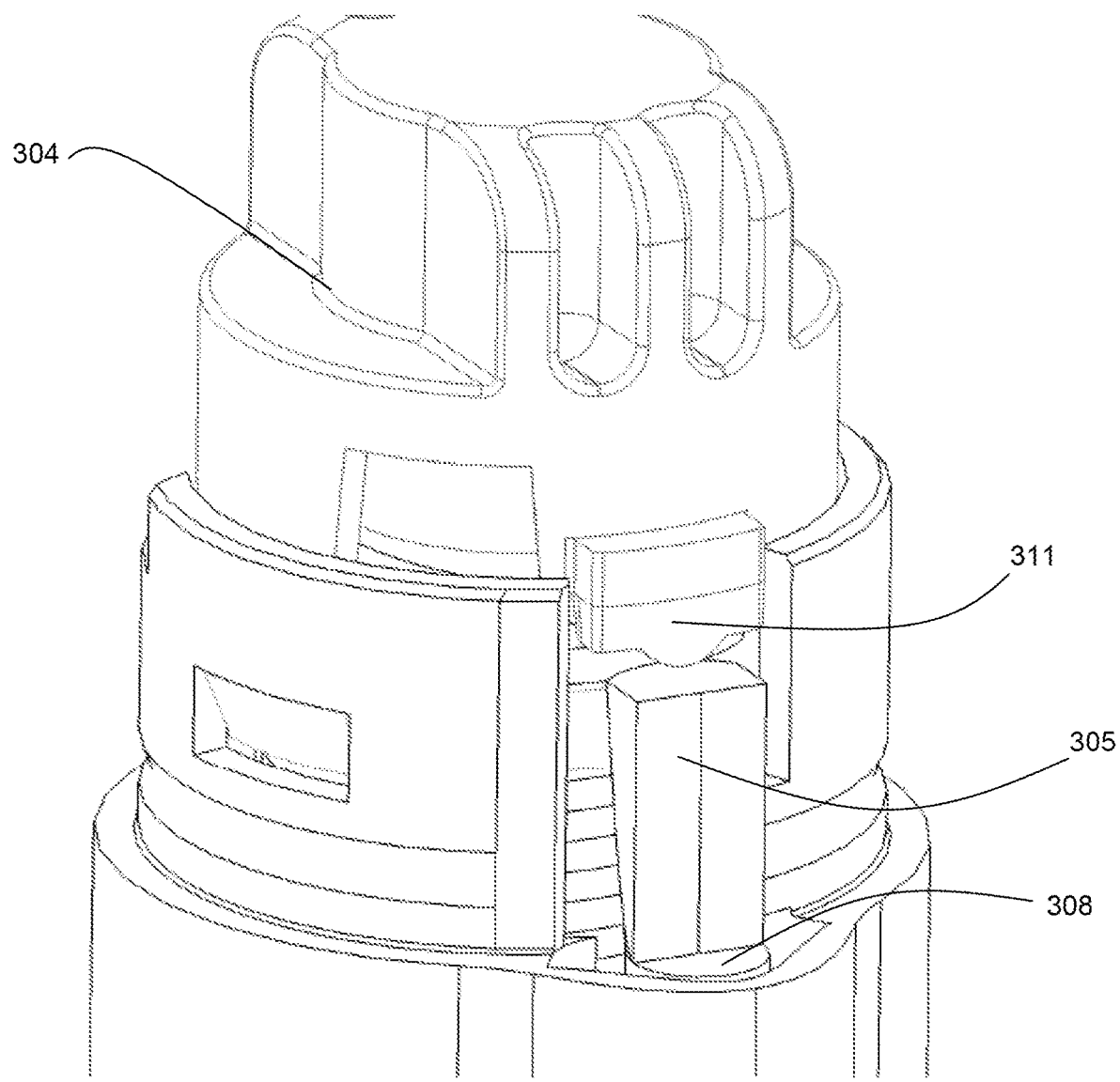
FIG. 11 shows a close up perspective view of the distal end of the auto-injector of FIG. 8.

FIG. 11 shows a close up view of the trigger 304 and trigger lock 305. The trigger 304 has a lip 311 that abuts the trigger lock 305, and prevents downward motion of the trigger 304. When the boot 312 is removed using the boot remover 302, the axial motion of the peg 306 causes the rod 308 to rotate due to the interaction between the peg 306 and helical track 310. The trigger lock 305, being connected to the rod 308, also rotates.

Figure 12:
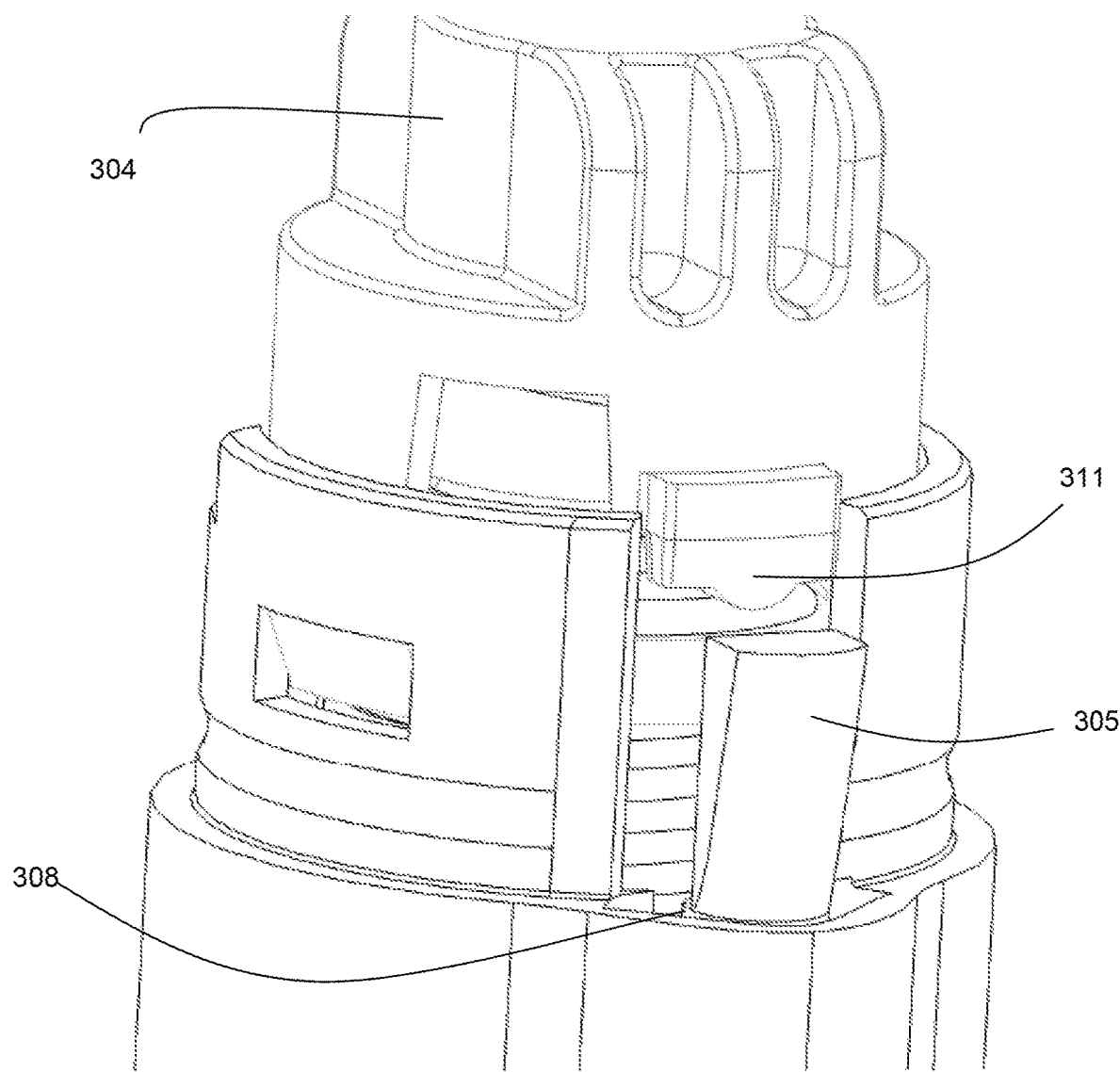
FIG. 12 shows a further close up perspective view of the distal end of the auto-injector of FIG. 8.
Figure 13:
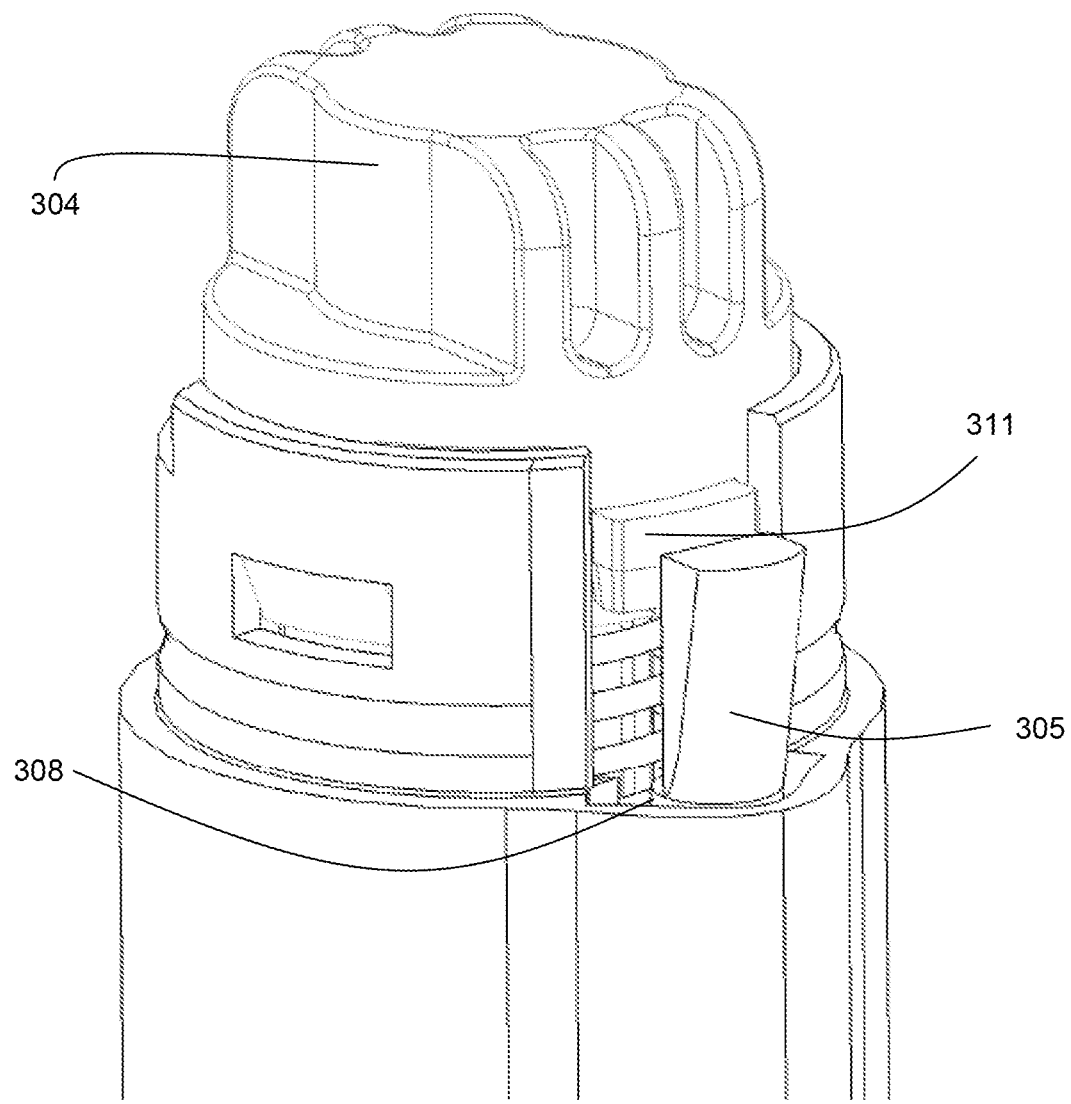
FIG. 13 shows a further close up perspective view of the distal end of the auto-injector of FIG. 8.

FIG. 12 shows a close up view of the trigger 304 and trigger lock 305 after the boot remover 302 has been removed. The trigger lock 305 no longer blocks the path of the lip 311, allowing the trigger 304 to be freely pushed downwards, activating the auto-injector. FIG. 13 shows the trigger 304 following actuation.

The helical linkage auto-injector 301 cannot be fired while the boot remover 302 is still in place. As the boot remover 302, along with the boot 312, is removed, the trigger lock 305 is disengaged. A user can then press the trigger 304 and activate the auto-injector 301.

With reference to FIGS. 14 to 17, there will now be described a fourth embodiment, referred to here as the "spring loaded lock auto-injector".

Figure 14:
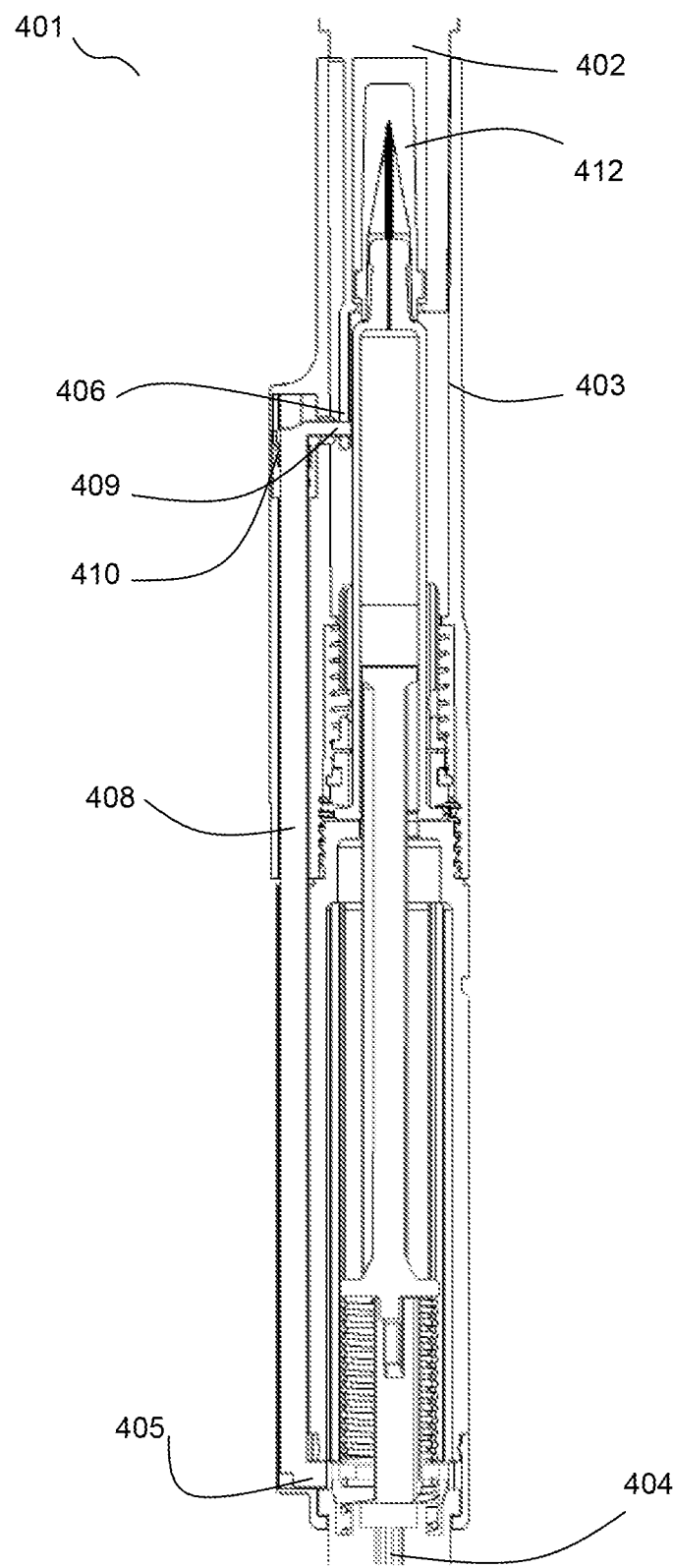
FIG. 14 shows a cross-section through an auto-injector according to a fourth embodiment.

FIG. 14 shows a cross sectional view of a spring loaded lock auto-injector 401, comprising a boot remover 402, boot 412, housing 403, trigger 404 and trigger lock 405. The boot remover 402 has a latch 406 and one or more keys 407 (not shown). The housing has one or more a linear, axially extending tracks (not shown) for engaging with the keys 405. This arrangement restricts rotation of the boot remover 402 prior to removal. Any number of ways can be used to prevent rotation of the boot remover 402 while attached to the spring loaded lock auto-injector 401.

Figure 15:
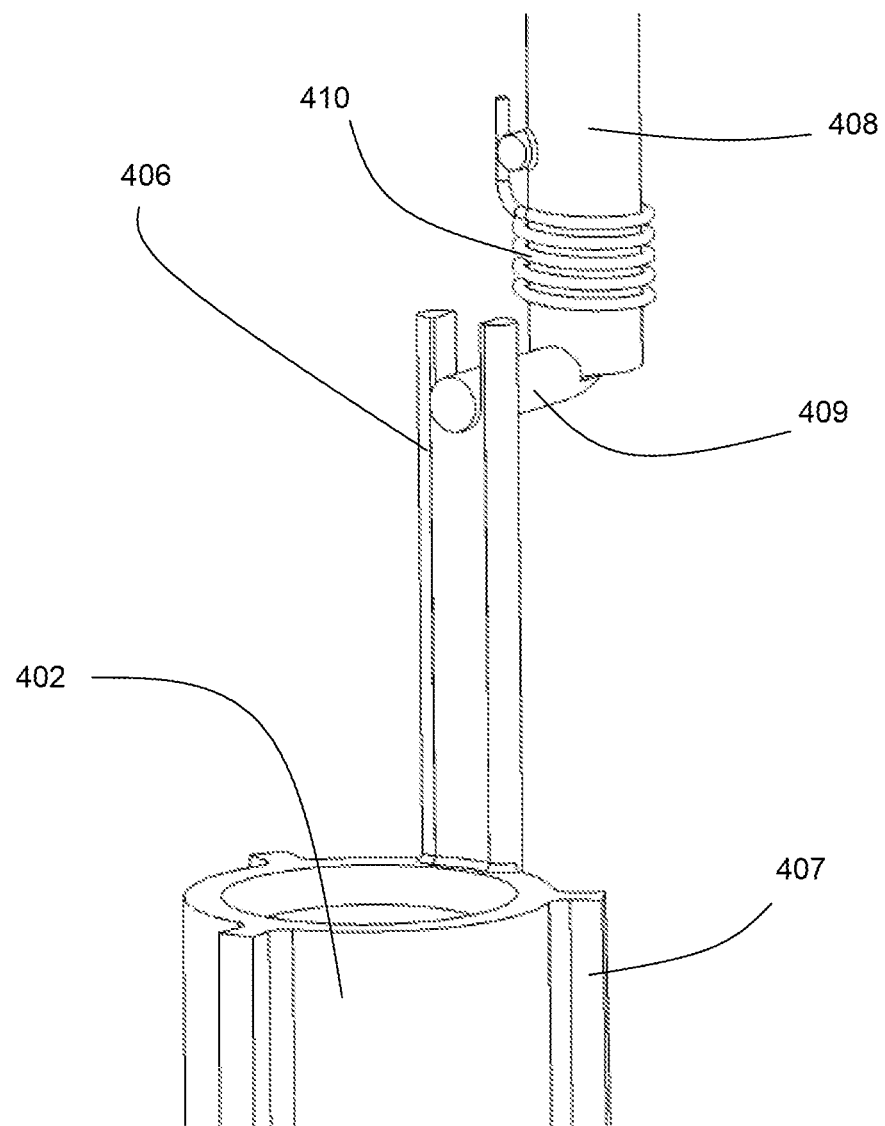
FIG. 15 shows a perspective view of a boot remover engaging with a rod according an example of the fourth embodiment.

The housing 403 contains a rod 408 with a pin 409 for engaging with the latch 406. The housing 403 also contains a torsion spring 410 that connects to the rod 408, providing a torque to the rod 408 when the rod is rotationally displaced from a given orientation. At one end of the rod 408 there is a trigger lock 405 for preventing actuation of the trigger 404. The trigger lock 405 is shaped such that, in one orientation, the trigger 404 cannot be activated, but, when the trigger lock 405 is rotated by 180 degrees, the trigger 404 can be activated. This may be facilitated by a stepped feature formed in the trigger lock 405. In the auto-injector's unarmed state, the rod is rotationally displaced such that a torque is applied to the rod 408 by the torsion spring 410, the rod 408 being held in place by the pin 409 being engaged with the latch 406. A perspective view of the latch and pin is shown in FIG. 15.

Figure 16:
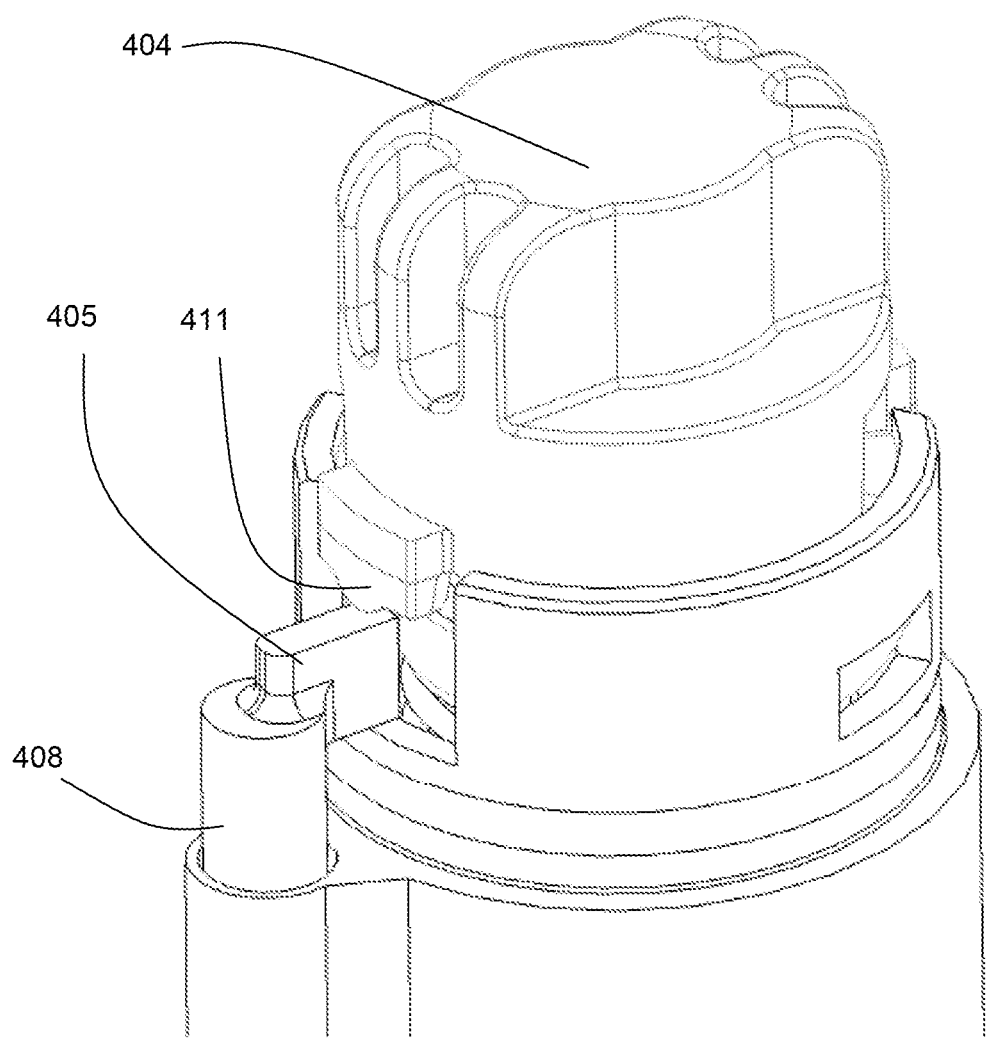
FIG. 16 shows up perspective view of the distal end of the auto-injector of FIG. 14.

FIG. 16 shows close up view of the trigger 404 and trigger lock 405 in an unarmed position. The trigger 404 has a lip 411 that abuts the trigger lock 405, preventing downward motion of the trigger 404.

When the boot remover 402 is removed, the pin 409 disengages with the latch 406, allowing the rod 408 and trigger lock 405 to rotate due to the torque applied by the torque spring 410. When the rod 408 and trigger lock 405 reach their final position, the trigger lock 405 no longer prevents the trigger 404 from being pressed.

Figure 17:
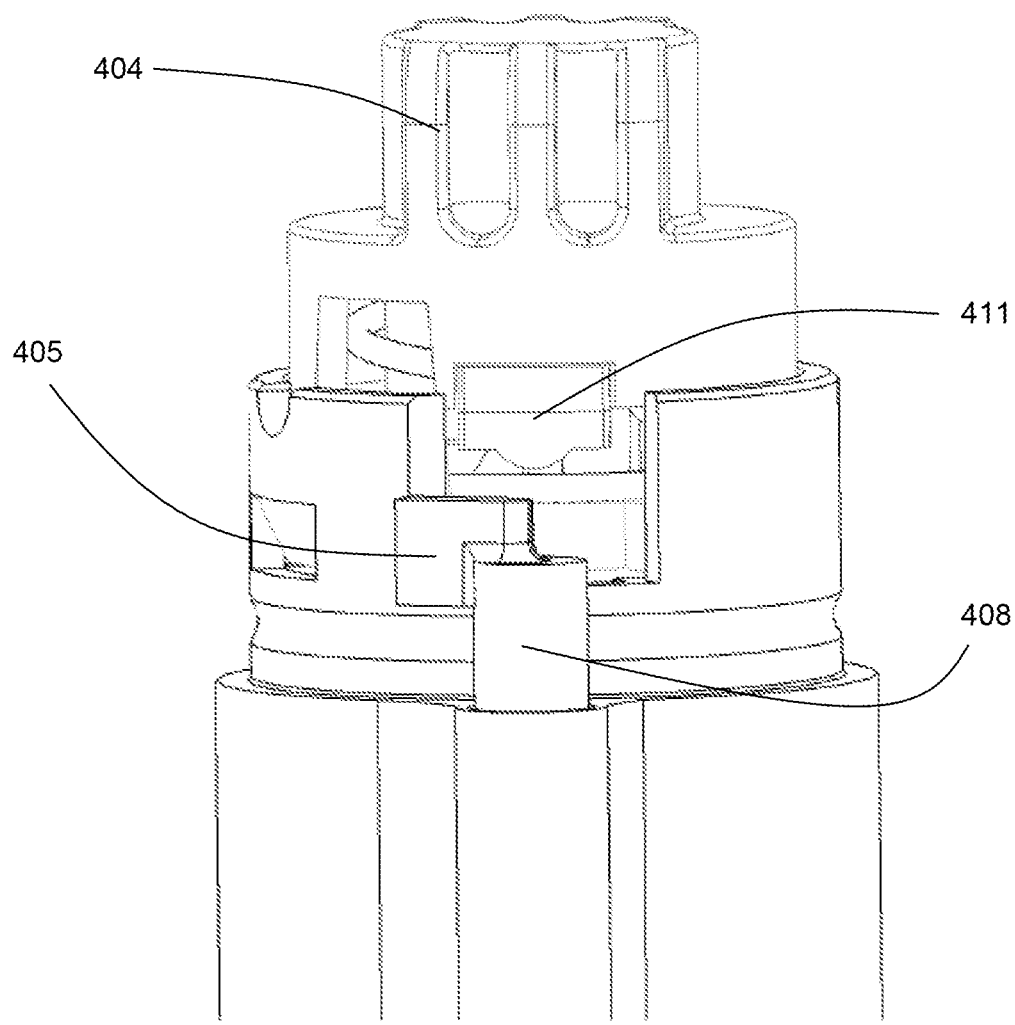
FIG. 17 shows a side view of the distal end of the auto-injector of FIG. 14.

FIG. 17 shows a close up of the trigger 404 and trigger lock 405 in an armed position. It will be apparent that rotation of the rod 408 has caused the trigger lock 405 to be rotated such that it no longer blocks the path of the lip 411, allowing the trigger 404 to be freely pushed downwards, activating the auto-injector 401.

The trigger lock in the helical linkage auto-injector and the spring loaded lock auto-injector have been described as having a trigger lock (305; 405) that is arranged to abut the trigger, preventing axial motion of the trigger (304; 404). It is noted that other trigger prevention mechanisms may be used instead. For example, the trigger lock may be a cover that prevents access to the trigger, wherein rotation of the rod causes the cover to move to into a position such that it does not prevent access to the trigger.

Figure 18:
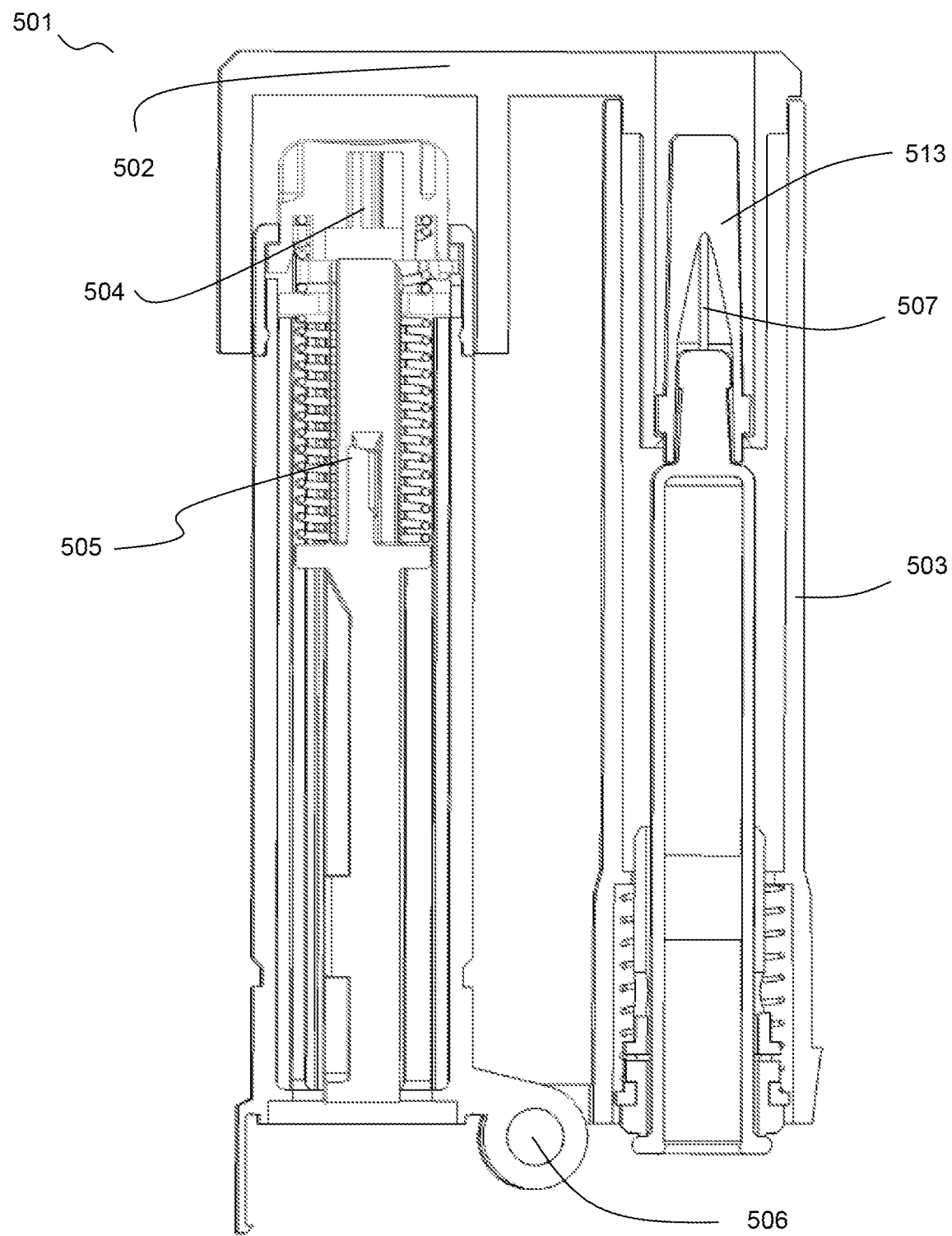
FIG. 18 shows a cross-section through an auto-injector according to a fifth embodiment.

With reference to FIGS. 18 to 26, there will now be described a fifth embodiment, referred to here as the "hinged auto-injector". FIG. 18 shows a cross sectional view of such a hinged auto-injector 501, comprising a boot remover 502, boot 514, syringe housing 503, trigger 504, firing mechanism housing 505, hinge 506 and needle 507. When folded, the hinged auto-injector 501 is in an unarmed position, with the boot remover 502 covering both the trigger 504 and the needle 507. In order to use the hinged auto-injector 501, the boot remover 502 must first be removed. The hinged auto-injector 501 can then be unfolded into a firing position.

Figure 19:
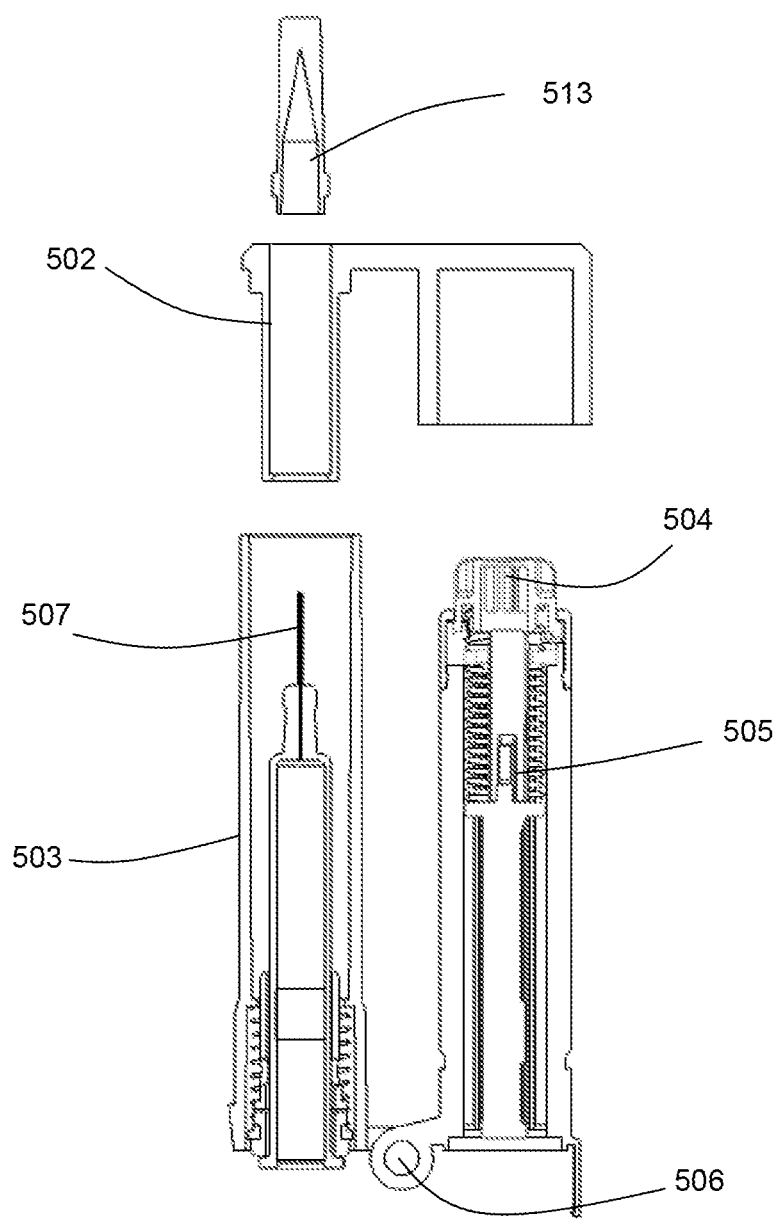
FIG. 19 shows a cross-section through the auto-injector of FIG. 18, with a boot remover removed.
Figure 20:
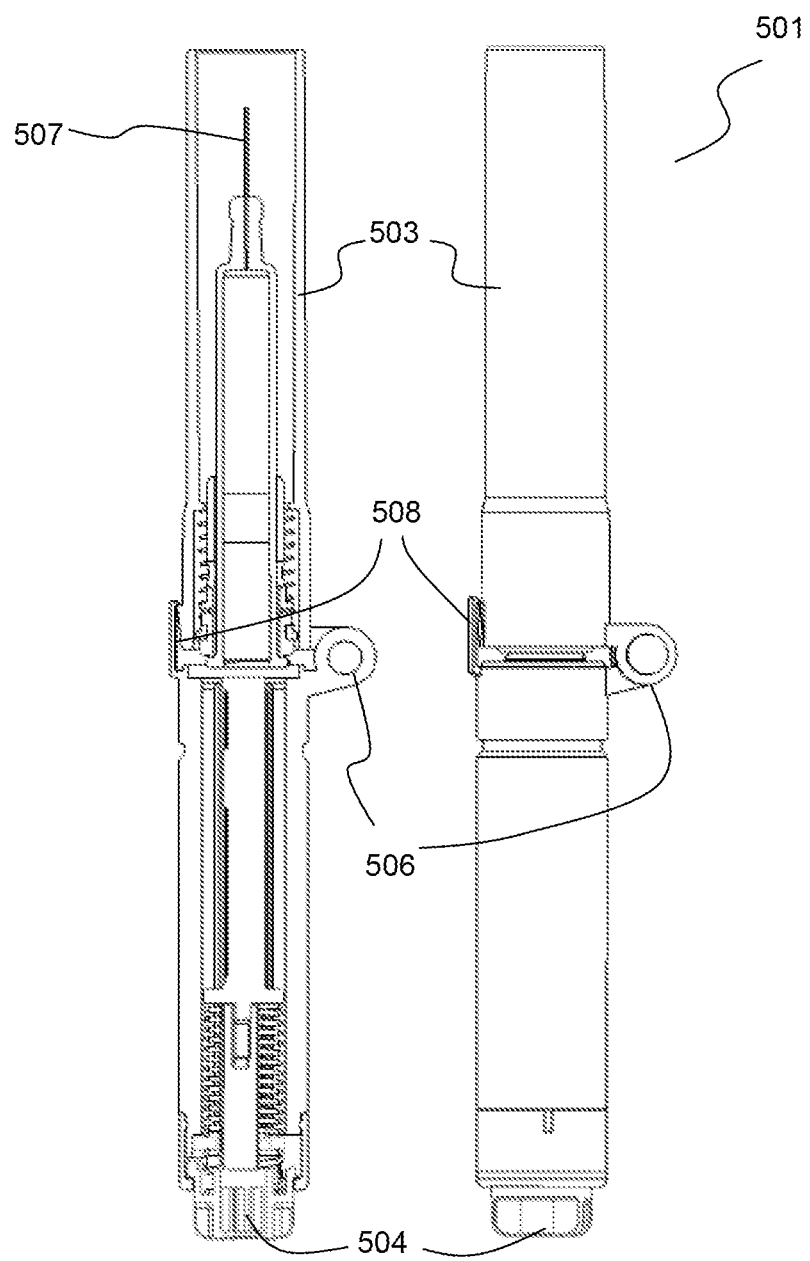
FIG. 20 shows a cross-section through the auto-injector of FIG. 18, and a side view of said auto-injector.

FIG. 19 shows the hinged auto-injector 501 with the boot remover 502 and boot 513 removed, but still in the folded configuration. FIG. 20 shows the hinged auto-injector 501 unfolded, as both a cross-section and in plan. A latch 508 may be used to lock the hinged auto-injector 501 in the unfolded position.

Figure 21:
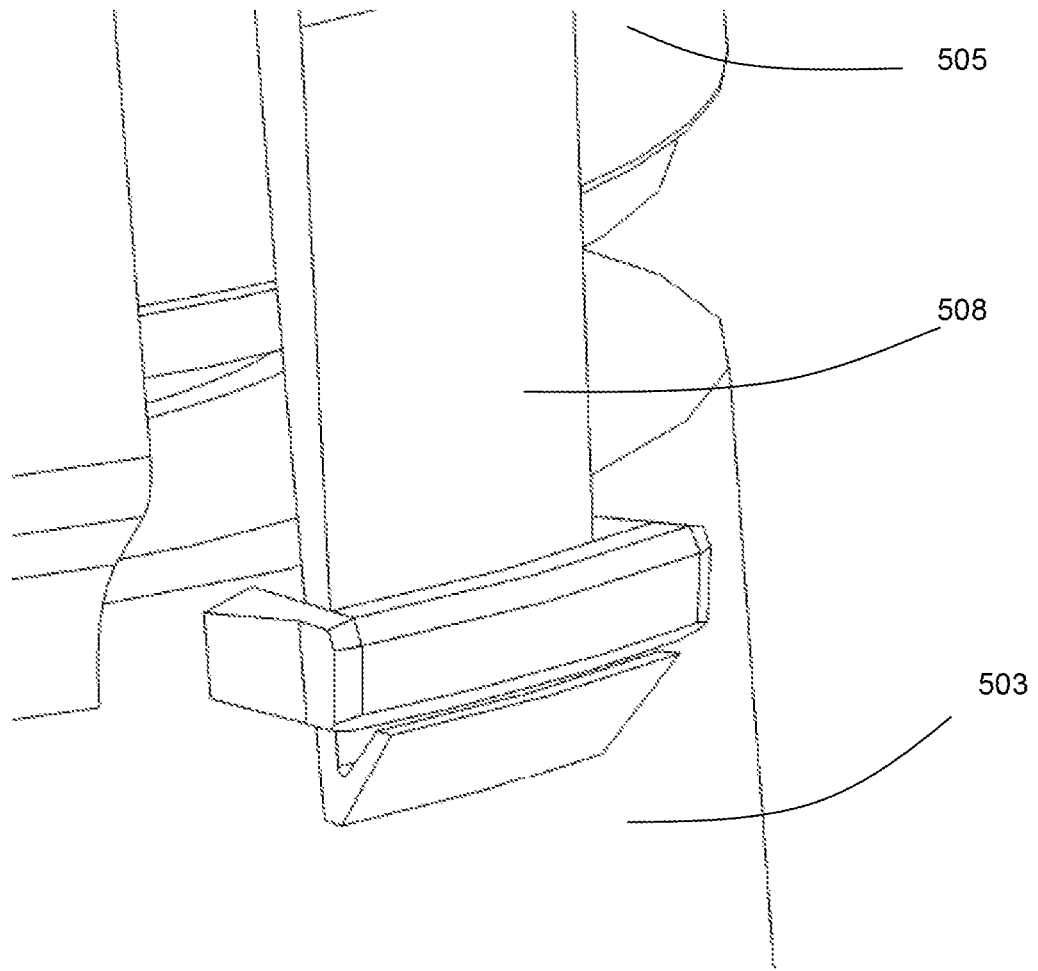
FIG. 21 shows a perspective view of a latch according to an option of the fifth embodiment.

FIG. 21 shows a close up view of the latch 508. Note that the latch 508 may reside on either the firing mechanism 505 or the housing 503. Other suitable mechanisms for locking the hinged auto-injector 501 in position will be readily apparent.

Figure 22:
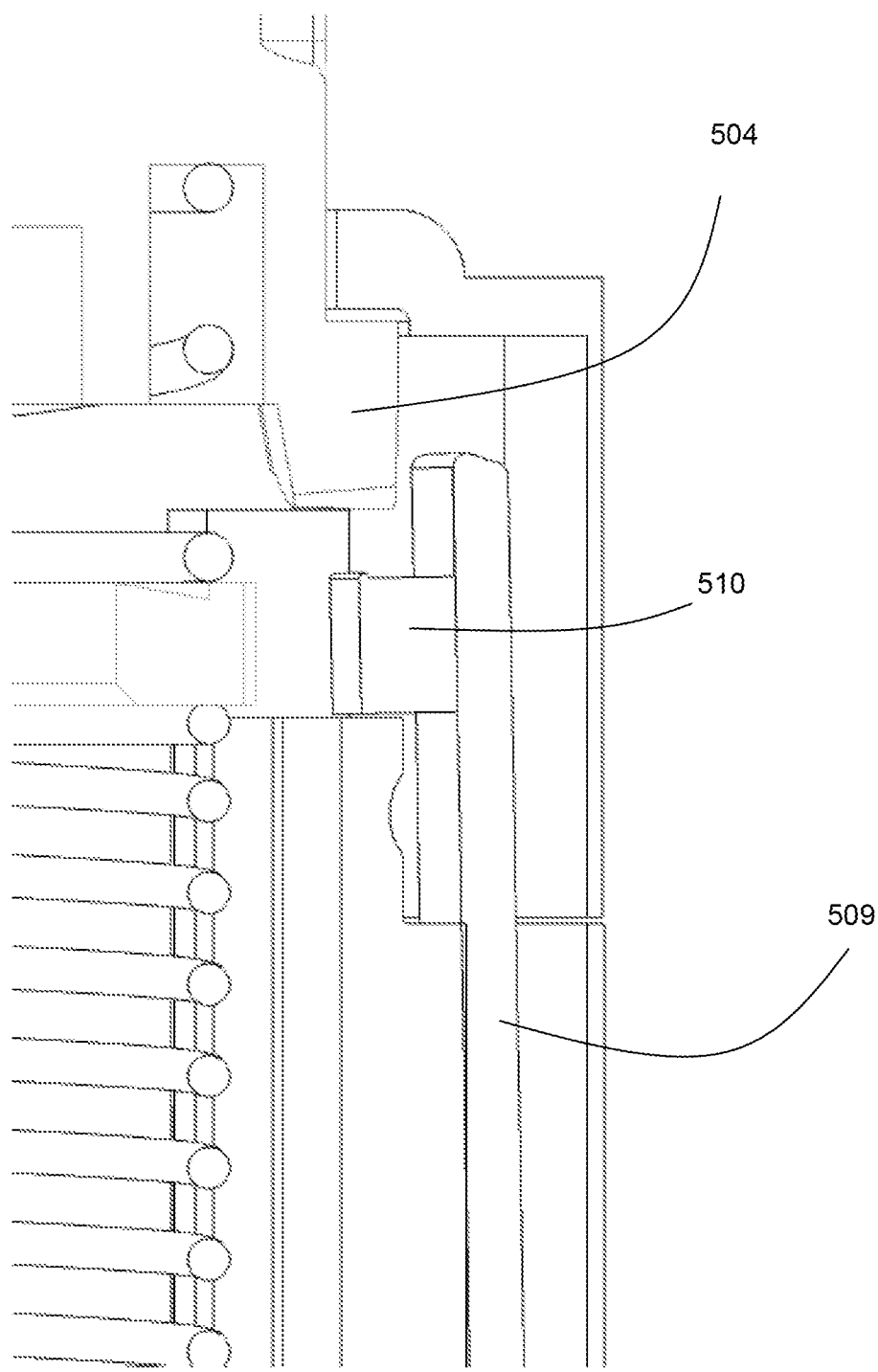
FIG. 22 shows a cross-section view of a trigger lock according to an option of the fifth embodiment.
Figure 23:
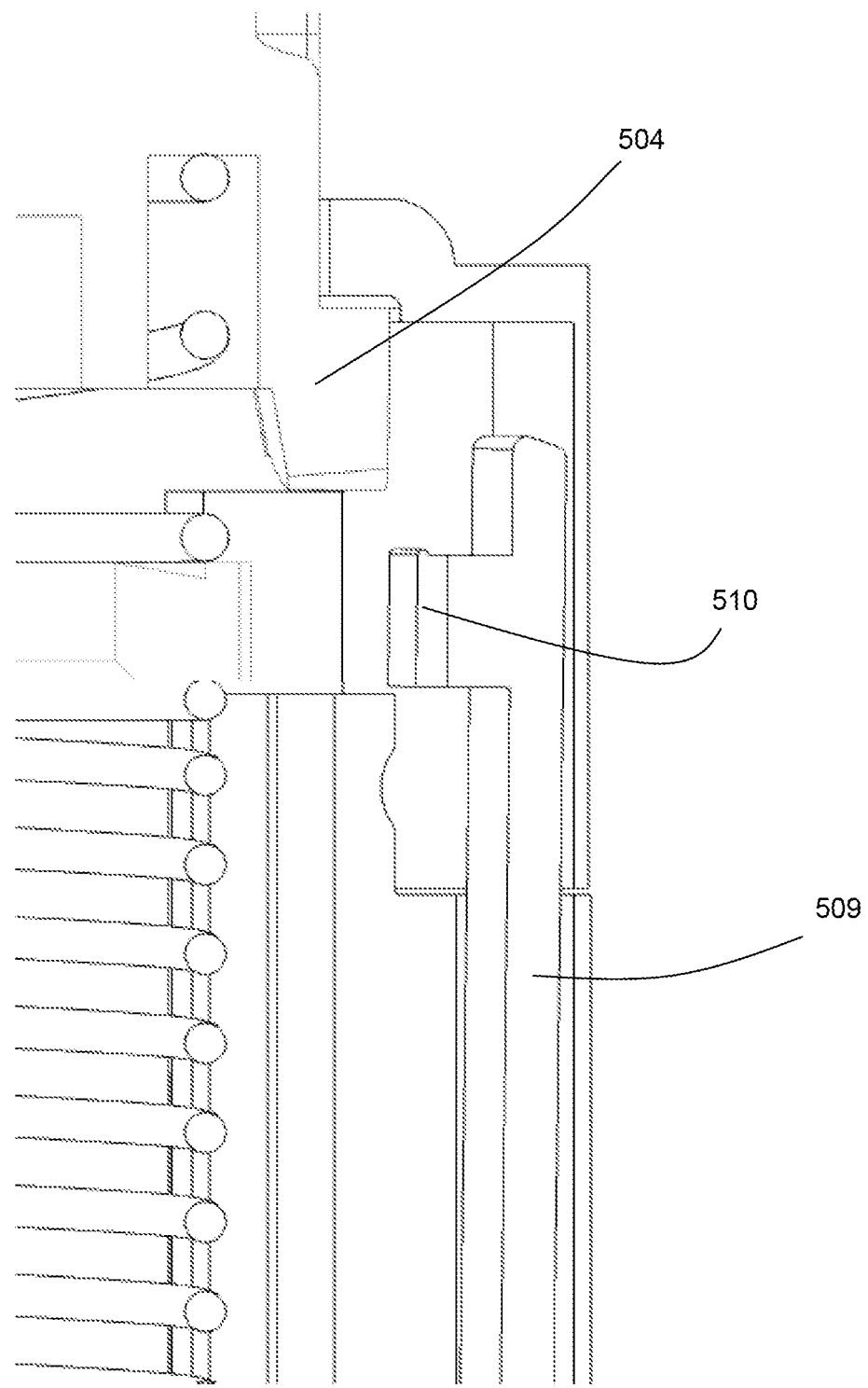
FIG. 23 shows a cross-section view of a trigger lock according to an option of the fifth embodiment in a different configuration.

The hinged auto-injector 501 may further comprise a mechanism that prevents actuation of the trigger 504 before the hinged auto-injector 501 has been fully unfolded. An example of such a mechanical interlock comprises a trigger lock comprising an elongate plate 509, shown in FIG. 22. The elongate plate 509 features a boss 510 for preventing downward motion of the trigger 504: FIG. 22 illustrates the "locked" position. The elongate plate 509, upon unfolding of the auto-injector, is caused to pivot about a central pivot axis from a position in which downward motion of the trigger 504 is prevented into one in which downward motion of the trigger is possible. FIG. 23 shows the elongate plate 509 in an unlocked position after unfolding of the device.

Figure 24:
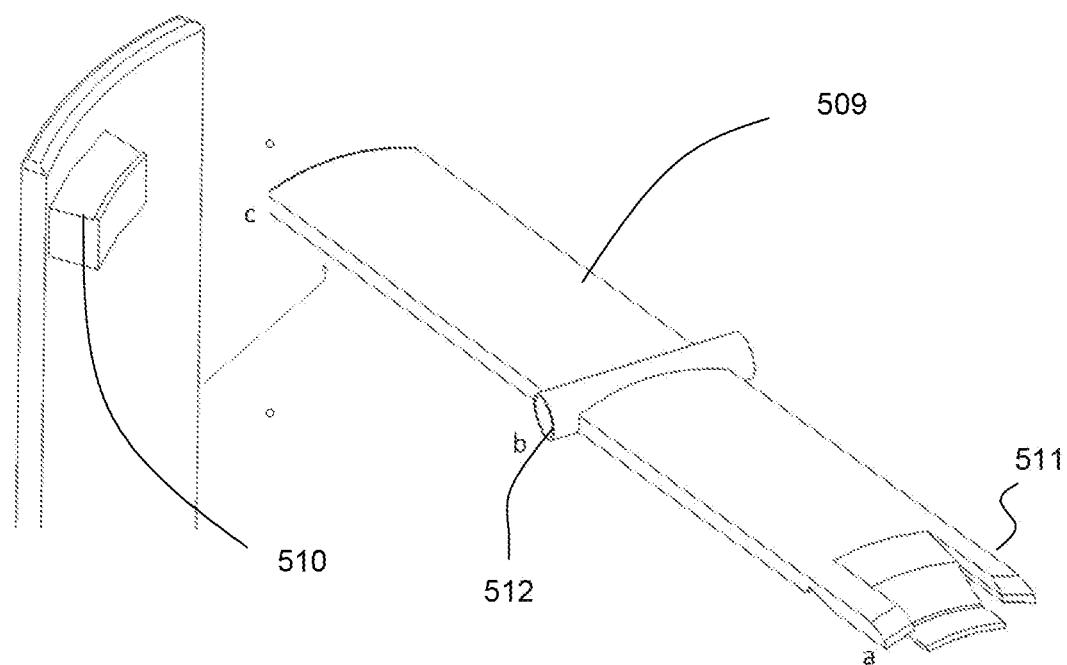
FIG. 24 shows a perspective view of a trigger lock according to an option of the fifth embodiment.
Figure 25:
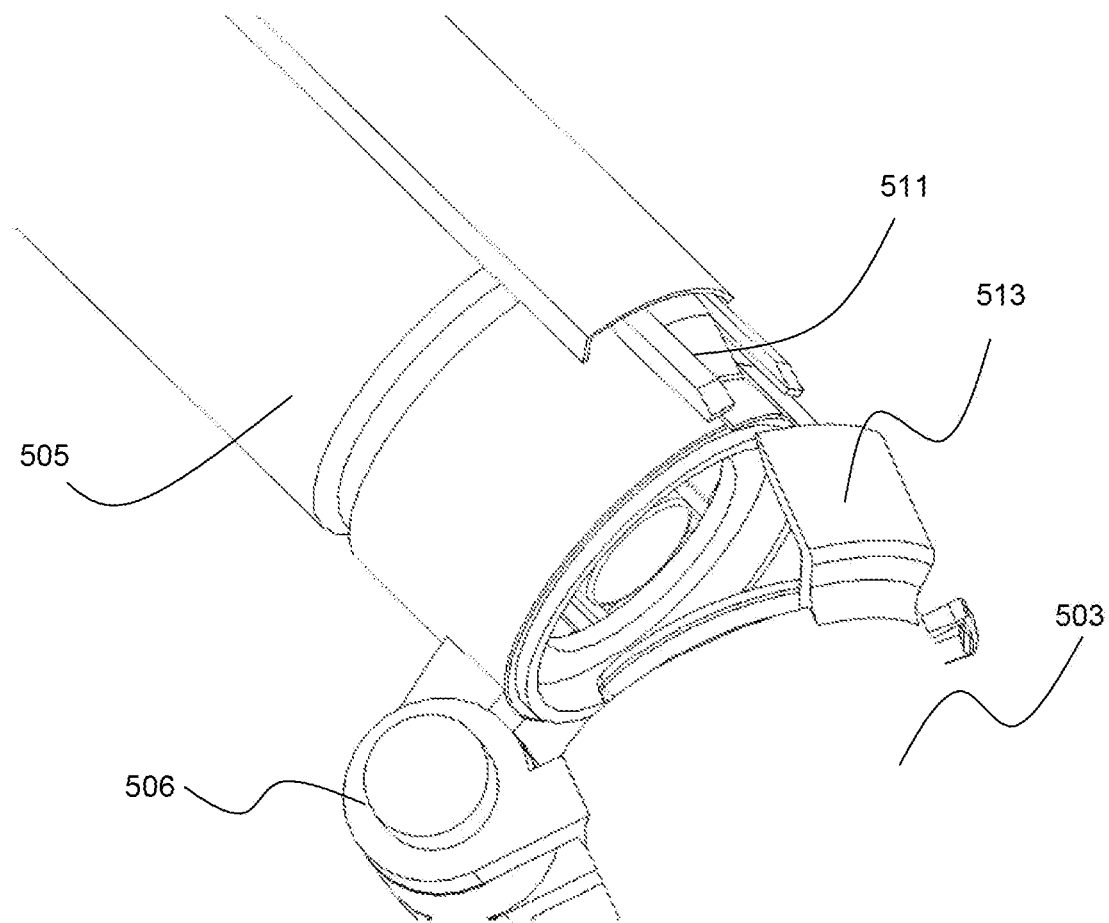
FIG. 25 shows a close up perspective view of the auto-injector of FIG. 18.
Figure 26:
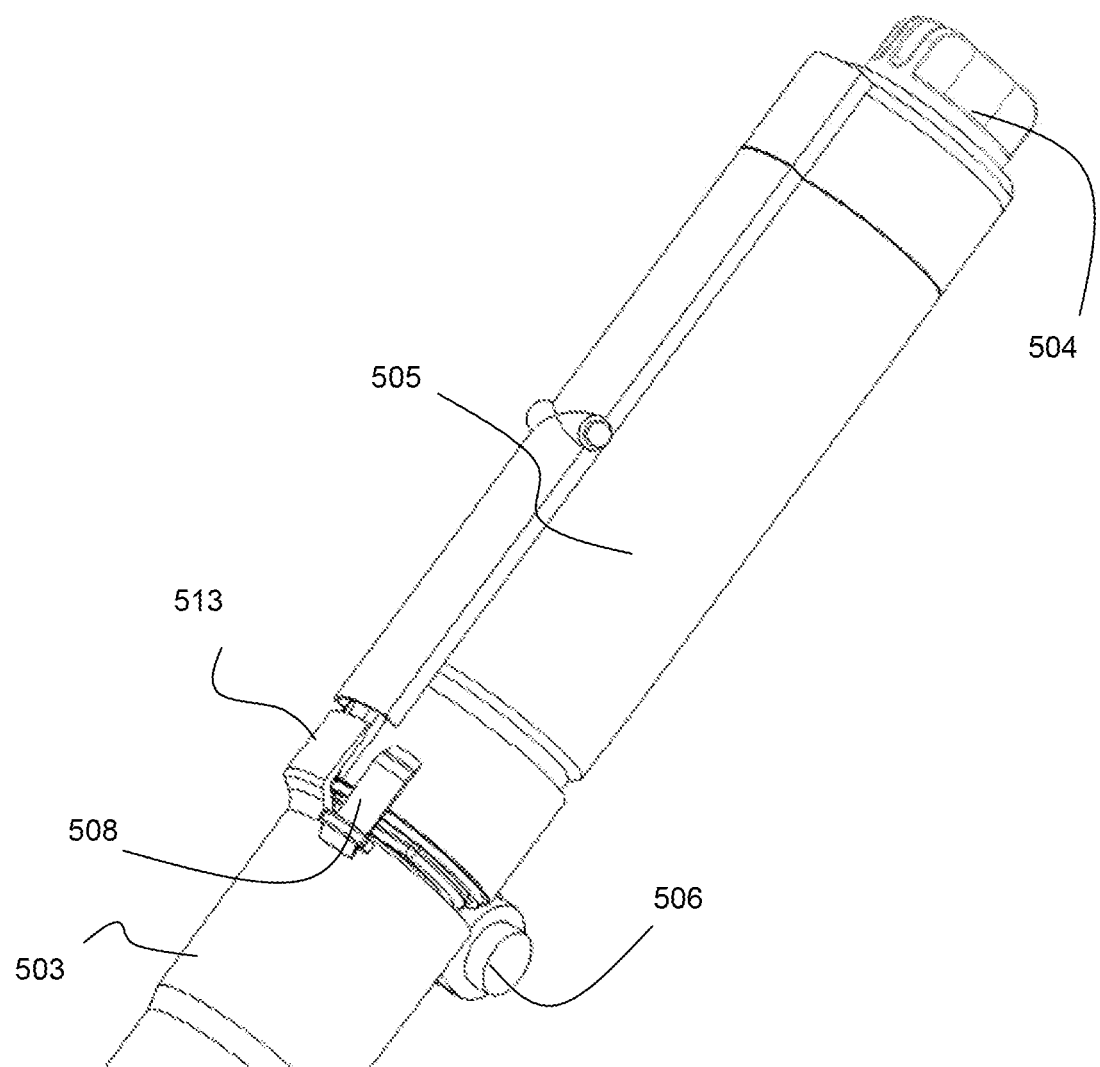
FIG. 26 shows a perspective view of the auto-injector of FIG. 18.

The elongate plate 509 is shown in more detail in FIG. 24. A front end of the trigger lock features an angled face 511 that acts as a spring and holds the elongate plate 509 in a locked position. The elongate plate 509 is mounted on a central pivot axle 512. As shown in FIG. 25, interaction with a second latch 513 on the housing 503 causes the angled face 511 to be pressed into the firing mechanism housing 505. This action causes the elongate plate 509 to pivot about the pivot axle 506, causing the boss 510 to move clear of the path of the trigger 504. FIG. 26 shows the hinged auto-injector 501 in a locked position, with the elongate plate 509 disengaged, and the latch 508 engaged.

With reference to FIGS. 27 to 30, there will now be described a sixth embodiment, referred to here as the "floating auto-injector". FIG. 27 shows a cross sectional view of such a floating auto-injector 601, comprising a boot remover 602, housing 603, and trigger 604 attached to the housing 603. The housing 603 houses a syringe, needle 609, and firing mechanism, which are not shown FIG. 27. The floating auto-injector 601 also comprises an outer casing 605, within which the housing 603 sits. The housing 603 is axially movable with respect to the outer casing 605.

The outer casing 605 has a first opening located at a proximal end and a second opening located at a distal end. The first opening is of sufficient size to allow the proximal end of the housing to pass through. The second opening is of sufficient size to allow the trigger to pass through. A spring 606 acts between the housing 603 and the outer casing 605 to bias the housing 603 in a distal direction.

The boot remover 602 is arranged to remove the boot 610 and further arranged such that when it is attached to the housing 603, the boot remover 602 holds the housing 603 forward in a first proximal position. While the housing 602 is held forward in the first position, the trigger 604 is held within the outer casing 605, and access to the trigger 604 is restricted. The floating auto-injector 601 may also comprise an elastic membrane 607 which covers the distal opening, preventing access to the inside of outer casing 605.

FIG. 28 shows the floating auto-injector 601 once the boot remover 602 has been removed. With the boot remover 602 no longer holding the housing 603 in place, the spring 606 pushes the housing 603 distally to a second position, such that the trigger 604 extends through distal opening, stretching the elastic membrane 607, and making the trigger 604 accessible to a user.

When the floating auto-injector 601 is not pressed against the user's skin, pressing the trigger 604 pushes the housing into the outer casing 605 such that the proximal end of the housing 604 exits the proximal end of the outer casing 605. The housing 604 is moved towards its first position, until the trigger 604 is no longer accessible. The force required to move the trigger 604 relative to the housing 603 is greater than the force required to move the housing 603 relative to the outer casing 605. Therefore, pushing the trigger 604 moves the housing 603 through the outer casing 605, and does not activate the floating auto-injector 601. This is shown in FIG. 29.

FIG. 30 shows the floating auto-injector 601 when the outer casing 605 is pressed against the skin 608. By applying pressure to the trigger 604 in a proximal direction, the proximal end of the housing 603 is pressed against the skin 608. With both the housing and outer casing 605 pressed against the skin, the two cannot move relative to one another, and so the force applied to the trigger 604 axially moves the trigger 604 relative to the housing 603, activating the floating auto-injector 601.

Figure 31:
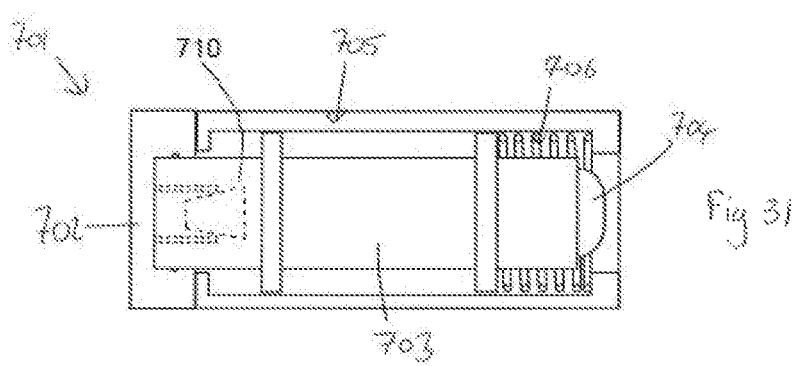
FIG. 31 shows a cross-section view of an auto-injector according to a seventh embodiment.
Figure 32:
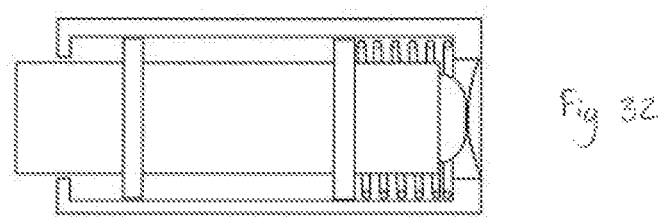
FIG. 32 shows a cross-section view of the auto-injector of FIG. 31 with a boot remover removed.
Figure 33:
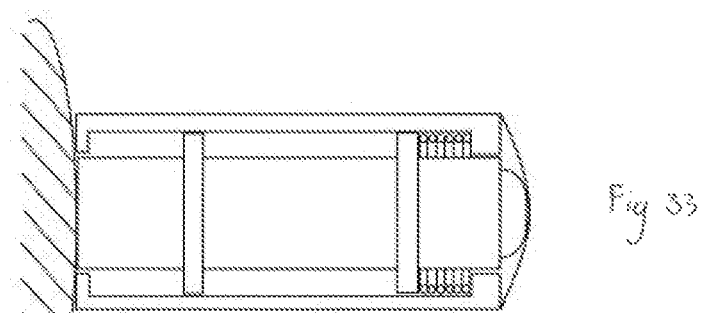
FIG. 33 shows a cross-section view of the auto-injector of FIG. 31 when pressed against the skin.
Figure 34:
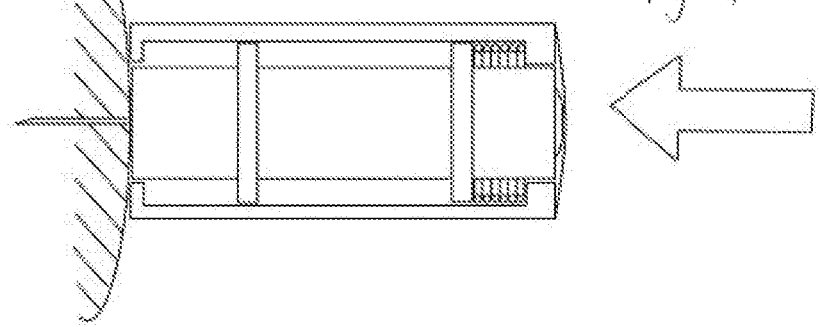
FIG. 34 shows a cross-section view of the auto-injector of FIG. 31 being activated.

FIGS. 31 to 34 show a seventh embodiment, the seventh embodiment being an alternative arrangement of the floating auto-injector embodiment. The alternative floating auto-injector 701 is structurally similar to the floating auto-injector 601, but whereas the floating auto-injector 601 has a spring 601 that urges the housing 603 distally with respect to the outer casing 605, the alternative floating auto-injector 701 has a spring 706 which urges the housing 703 proximally with respect to the outer casing 705. When urged forward by the spring 706, access to the trigger 704 is restricted, as shown in FIGS. 31 and 32. In order to access the trigger 704, a proximal ending of the housing 703 must be pressed against a user's skin in order for the housing to move rearward relative to the outer casing 705, as in sixth embodiment. When the boot remover 702 that is configured to remove the boot 710 is attached, the boot remover 702 covers a proximal end of the outer casing 705, such that the housing 703 cannot be pressed against the user's skin. Therefore, in order to activate the device 701, the user must first remove the boot remover 702, exposing the proximal end of the housing 703, and then press the proximal end of the housing 703 against the skin, such that the trigger 704 becomes accessible. The device can then be activated by pressing the trigger.

With reference to FIGS. 35 to 39, there will now be described a eighth embodiment, referred to here as the "toothed wheel auto-injector". FIG. 35 shows a cross sectional view of such a toothed wheel auto-injector 801, comprising a boot remover 802, housing 803, trigger 804 and skin sensor 805. The housing is arranged to house a syringe carrying needle and force applicator (not shown). When the boot remover 802 is attached to the device 801, the boot remover 802 abuts the trigger 804, preventing the trigger 804 from being displaced relative to the housing 803. FIG. 36 shows the toothed wheel auto-injector 801 following removal of the boot remover 802.

The toothed wheel auto-injector 801 further comprises a rotatable shaft 806 which is coupled to a plunger 807. The plunger 807 is coupled to the trigger 804 such that by pressing the trigger 804, the plunger is pushed into a bung of a syringe. The plunger 807 may be driven via a drive spring (not shown), or any other means.

The rotatable shaft 806 is connected to the plunger 807 by a flexible member 808, such as string. The rotatable shaft 806 has two toothed portions 809, 810 which extend circumferentially around the outer surface of the rotatable shaft 806. The toothed portions 809, 810 are arranged to engage with locking levers 811, 812, which prevent rotation of the shaft 806. When the shaft 806 is rotationally fixed, the plunger 807 is restricted from axially movement due to the connection via the flexible member 809. Alternatively, the flexible member 808 may be attached directly to the trigger 804, preventing axial movement of the trigger 804 when the locking levers 811, 812 are engaged.

The skin sensor 805 is arrange to extend beyond a proximal end of the housing 803, and further arranged such that when the skin sensor 805 is pressed against the skin, the skin sensor 805 is pushed into the housing 803. When pushed into the housing 803, the skin sensor 805 acts on the locking levers 811, 812 via legs 813, 814, disengaging the locking levers 811, 812 from the toothed portions 809, 810 of the shaft 806, allowing rotation of the shaft 806.

The locking levers 811, 812 are pivotally attached to the housing 803 via pivot points 814, 815. The pivot points 815, 816 are located between a part of the levers where the legs 813, 814 of the skin senor 805 act, and a part of the levers that engage with the toothed portions 809, 810. Therefore, when pressed against the skin, the skin sensor 805 causes the locking levers 811, 812 to pivot, disengaging them from the toothed portions 809, 810, and allowing the device 801 to be actuated. FIG. 37 shows the skin sensor having been pushed into the housing, such that the locking levers 811, 812 have pivoted about the pivot points 815, 816, disengaging from the shaft 806. FIG. 38 shows the trigger 804 being pushed into the housing. FIG. 39 shows alternative views of the plunger 807, and shaft 806.

Figure 40:
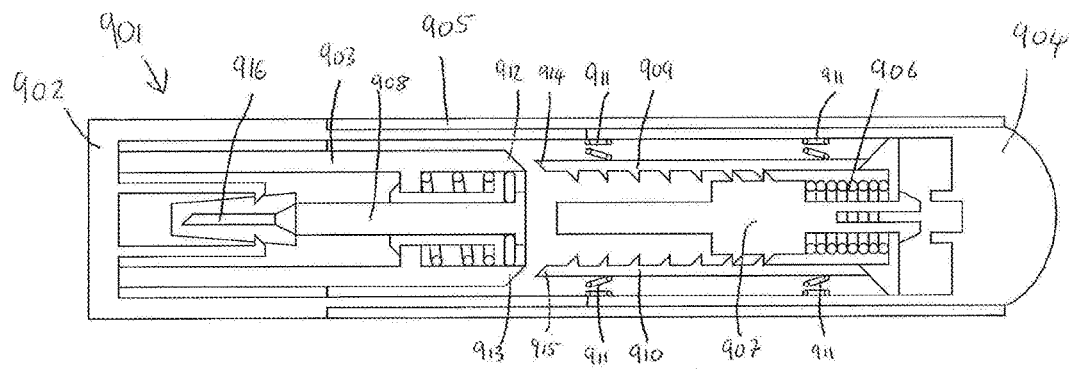
FIG. 40 shows a cross-section view of an auto-injector according to a ninth embodiment.

With reference to FIGS. 40 to 45, there will now be described a ninth embodiment, referred to here as the "toothed element auto-injector". FIG. 40 shows a cross sectional view of such a toothed element auto-injector 901, comprising a boot remover 902, housing 903, trigger 904 and outer casing 905.

Figure 41:
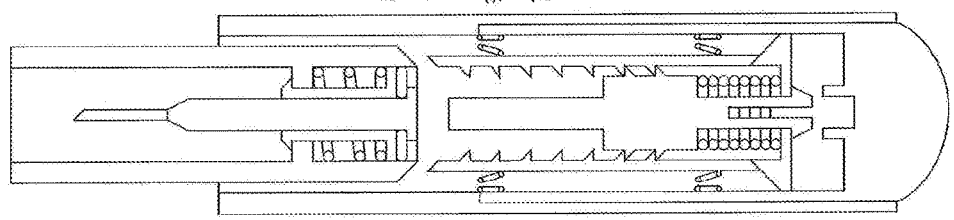
FIG. 41 shows a cross-section view of the auto-injector of FIG. 40 following removal of a boot remover.

The boot remover 902 abuts the trigger 904, prior to removal of the boot remover 902. This prevents the trigger 904 from being displaced relative to the outer casing 905 and/or the outer casing 905 to activate the device 901. FIG. 41 shows the boot remover 902 removed.

The housing 903 is located within the outer casing 905 and a part of the housing 903 protrudes from a proximal end of the outer casing 905, such that it can be pressed against the skin. The outer casing 905 comprises a drive spring 906 and plunger 907, for acting on a bung or plunger of a syringe 908 contained in the housing 903. Pressing the trigger 904 activates the drive spring 906, which drives the plunger 907.

Figure 42:
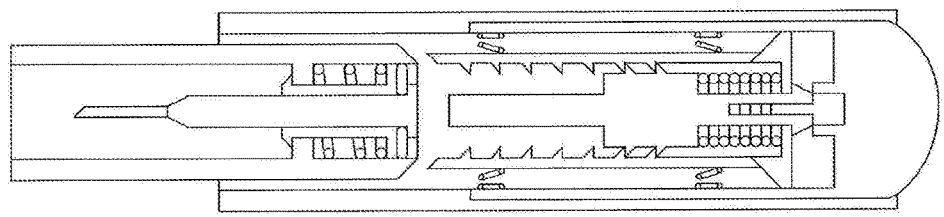
FIG. 42 shows a cross-section view of the auto-injector of FIG. 40 following removal of a boot remover.

The device 901 further comprises two locking elements 909, 910 axially fixed within the outer casing 905. The locking elements 909, 910 have interlocking teeth which engage with interlocking teeth on the plunger 907, preventing axial movement of the plunger 907. When the locking elements 909, 910 are engaged, the device 901 cannot be activated (FIG. 42).

Figure 43:
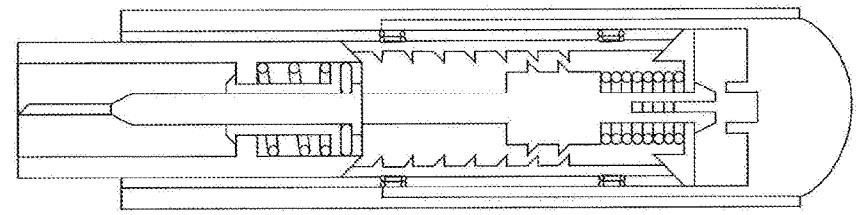
FIG. 43 shows a cross-section view of the auto-injector of FIG. 40 when pressed against the skin.

The housing 903 is axially moveable relative to the outer casing 905, and when pressed against the user's skin, the housing 903 is pushed into the outer casing 905 (FIG. 43).

The outer casing 905 comprises biasing springs 911 which bias the locking elements 909, 910 against the plunger 907 such that the teeth interlock. While teeth have been described, it will be understood by the skilled person that any interlocking feature may be used.

Figure 44:
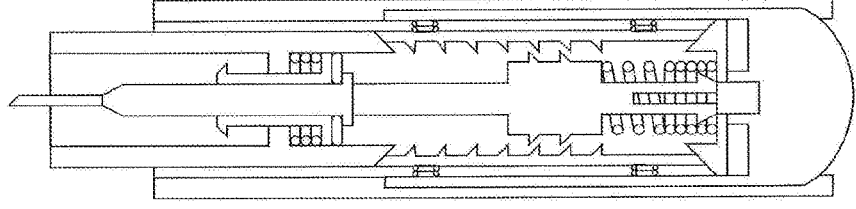
FIG. 44 shows a cross-section view of the auto-injector of FIG. 40 being activated.
Figure 45:
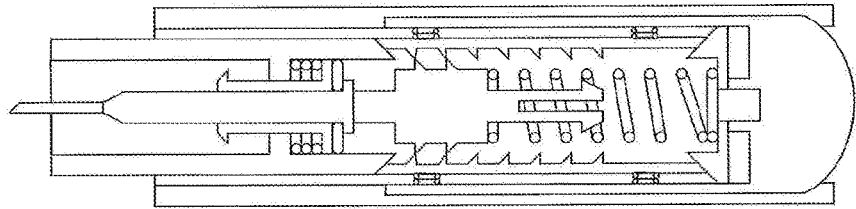
FIG. 45 shows a cross-section view of the auto-injector of FIG. 40 after activation.

The housing 903 has two angled surfaces 912, 913 which interact with two angled surfaces 914, 915 on the locking elements 909, 910, when the housing 903 is pressed into the outer casing 905. These angled surfaces cause the locking elements to be radial displaced, disengaging them from the plunger 907 (FIG. 43-45).

Therefore, the boot remover must first be removed and then the device 901 pressed against the skin before pressing the trigger 904 activates the device 901, driving a needle 916 into a user and dispensing medicine contained in the syringe 908.

With reference to FIGS. 46 to 50, there will now be described a tenth embodiment. FIG. 46 shows a cross sectional view of an auto-injector 1001 according to the tenth embodiment. The auto-injector 10001 comprises a boot remover 1002 for removing a boot 1002a, housing 1003, trigger 1004 and skin sensor 1005. The housing 1003 houses a syringe carrying medicine, a needle, and drive mechanism (not shown) for driving the needle into a user's skin, and dispensing the medicine.

The skin sensor 1005 extends proximally from the housing 1002, and is arranged to be pressed against the user's skin. The boot remover 1002 covers the skin sensor 1005 such that the skin sensor 1005 cannot be pressed against the skin. With the boot remover 1002 removed (FIG. 47), the skin sensor 1005 can be pressed against the skin. The skin sensor 1005 has an elongated leg 1006 which abuts a corresponding elongated leg 1007 on the trigger 1004. The abutment prevents the trigger 1004 from being axially displaced.

The skin sensor 1005 further comprises a helical keyway 1008 which engages with a boss 1009 on an inner surface of the housing 1003. When the skin sensor 1005 is pressed against the skin, the skin sensor rotates into the housing due to the boss 1009 following the helical keyway 1008 (FIGS. 48 and 49). This allows the elongated leg 1006 of the skin sensor 1005 to disengage from the elongated leg 1007 of the trigger 1004, thereby allowing displacement of the trigger.

With reference to FIGS. 51 to 53, there will now be described an eleventh embodiment. FIG. 51 shows a cross sectional view of a distal end of an auto-injector 1101 according to the eleventh embodiment. The auto-injector 11001 comprises a boot remover (not shown) for removing a boot, housing 1102, trigger 1103 and skin sensor 1104. As with the eighth embodiment, the skin sensor 1104 is arranged to be pressed against the skin, such that it enters the housing 1102. The boot remover is arranged such that, prior to removal, it covers a proximal end of the skin sensor 1104, preventing it from being pressed against the skin and into the housing 1102. The trigger 1103 is prevented from axial movement in the proximal direction due to an abutment between the trigger 1103 and two flexible legs 1105, 1106 fixed on the inside of the housing 1102.

When the boot remover is removed, the skin sensor 1104 is pressed against the skin, such that it moves axially into the housing 1102. The a distal end of the skin sensor 1104 pushes against the flexible legs 1105, 1106, causing them to deform (FIG. 52). Once deformed, the flexible legs 1105, 1106 no longer abut the trigger 1103, allowing activation of the device 1101 (FIG. 53).

With reference to FIGS. 54 to 59, there will now be described a twelve embodiment. FIG. 55 shows a trigger 1201 for activating an automatic injection device (not shown). The trigger 1201 has three latches 1202 which extend from the trigger 1201, and are arranged to project through slots 1203 of a housing 1204 of the auto-injector (FIG. 56). This engagement prevents actuation of the trigger 1201.

The auto injector has three release elements 1205 (a release element is shown in FIG. 54 from a side view and front view). The release elements 1205 have a de-latching portion 1206, which feature a raised, angled surface 1207 for engaging with the latch 1202 of the trigger 1201. The release elements extend beyond a proximal end of the housing 1204 and are arranged such that, when the auto-injector is pressed against the skin, the release elements 1205 are pushed into the housing 1204 and the de-latching portions 1206 engage with, and slide past, the latches 1205 so as to press the latches back through the slots 1203 and allow the trigger 1201 to be actuated (FIGS. 57 and 58).

The release elements 1205 are fixed to the housing 1204, and have integral spring elements 1207 between the attachment to the housing and the de-latching portion 1206. The spring elements 1207 are arranged to compress when the release elements 1205 are pressed against the skin. Any number of release elements may be used. The release elements 1205 are distributed evenly around a circumference having its centre along an axial direction of the housing 1204. This can be seen from FIG. 55, where the three latches 1202, which engage with the release elements 1205, are distributed evenly.

FIG. 59 shows a boot remover 1208 which removes the boot (not shown), and covers the release elements 1205. The boot remover 1208 must be removed before the release elements 1205 can be pressed against the skin.

With reference to FIGS. 60 to 63, there will now be described a thirteenth embodiment. FIGS. 60 to 63 show a top cross sectional view of an auto-injector of the thirteenth embodiment, and a partial cross sectional side view. The auto-injector 1301 of the thirteenth embodiment comprises a housing 1302 which houses a syringe and needle, and drive mechanism (not shown) for activating the device 1301; a trigger 1303 coupled to the housing 1302, and arranged to activate the drive mechanism; a boot remover 1304 for removing the boot and covering the proximal end of the device 1301; a skin sensor 1305 protruding proximally beyond the housing 1302 and an out casing 1306; and an elliptical flexible collar 1307 axially fixed to the housing 1302, and located between the trigger 1303 and the housing 1302.

The elliptical flexible collar 1307 is arranged to sit around a part of the trigger 1303, and prevent the trigger 1303 from being fully depressed when in a first configuration, preventing activation of the device 1301. In the first configuration the collar 1307 has a minor axis 1308 which is shorter than the diameter of an upper part of the trigger 1309. This prevents the trigger 1303 from being fully depressed into the housing 1302 (FIG. 60 shows the device 1301 with the boot remover 1304 attached, and 61 shows the device with the boot remover removed). Note that while the trigger is described as having a diameter, and the collar is describe as being elliptical, both may be any suitable shape such that deformation of the collar allows the trigger to pass through.

The skin sensor 1305 has an angled surface 1310 at its distal end. When the skin sensor 1305 is pressed against the skin (FIG. 62), it is moved into the outer casing 1306, and the angled surface 1310 pushes against the vertices defining the major axis, so as to deform the elliptical flexible collar 1307. The deformation causes the minor axis to increase in length, until the trigger 1303 is no longer blocked by the collar 1307. In this second configuration, the device can then be activated (FIG. 63). The boot remover 1304 covers the skin sensor 1305 prior to removal. Once removed, the skin sensor 1305 may be pressed against the skin.

With reference to FIGS. 64 to 68, there will now be described a fourteenth embodiment. FIGS. 64 to 68 show a cross section of an auto-injector of the thirteenth embodiment. The auto-injector 1401 comprises a housing 1402 housing a syringe, drive mechanism (not shown), and needle 1411; an outer casing 1403 within which the housing 1402 is located; a boot remover 1404 for removing a boot and covering the proximal end of the device 1401; and a trigger 1405.

The housing 1402 is contained within the outer casing 1403 and arranged to be axially moveable within the outer casing 1403. The drive mechanism within the housing 1402 is prevented from being released and activating the device 1401 by being connected to flexible member 1406 which is clamped in two places.

The auto-injector 1401 further comprises a spring 1407 which acts between the outer casing 1403 and the housing 1402 and biases the housing 1402 towards a proximal end of the outer casing 1403 such that a part of the housing 1402 protrudes from an opening of the proximal end of the outer casing 1403. When held in this forward position by the spring 1407, a part of the flexible element 1406 is clamped in a first clamped position 1408 between an outer surface of the housing 1402 and an inner surface of the outer casing 1403. When the housing 1402 is pressed against the skin, the housing 1402 moves into the outer casing 1403, which releases the clamp 1408 (FIG. 66).

The boot remover 1404 prevents the housing 1402 from being pressed against the skin, prior to removal.

The flexible element 1406 is further clamped in a second position by a butterfly valve 1409 coupled to the housing 1402. The trigger 1405 has two release pegs 1410, which engage with the butterfly valve 1409 when the trigger 1405 is displaced. This engagement opens the valve 1409, unclamping the flexible element 1406 from the second clamp (FIG. 67). The drive mechanism is no longer prevented from being released by the flexible member, and so the device 1401 is activated, driving the needle 1411 and medicine into the user's skin.

The device 1401 is a further arranged, such that when the housing 1402 is held in the forward position by the spring 1407, the butterfly valve 1409 is held in a position which is inaccessible to the release pegs 1410 of the trigger 1404. This is shown in FIG. 65, where the trigger 1405 is pressed into the housing, but does not reach the valves 1410. While not shown, the trigger 1405 has limited axial movement due to a structural stop, such as a ledge within the outer casing 1403.

It will be appreciated by the person of skill in the art that various modifications may be made to the above described embodiments without departing from the scope of the present invention. Furthermore, while several separate embodiments have been described, the skilled person will recognise that some of these embodiments may be combined.

The invention claimed is:

1. An automatic injection device for delivering a dose from a medicine-containing syringe, the injection device comprising:
    an outer casing comprising a first opening at a proximal end and a second opening at a distal end;
    a housing configured to contain the syringe, the housing being disposed within the outer casing and being axially movable within the outer casing, a proximal end of the housing being configured to pass through the first opening of the outer casing;
    a firing mechanism configured to apply a force to eject medicine from the syringe;
    a trigger coupled to the firing mechanism and configured to release the firing mechanism to cause an injection, the trigger being attached to the housing and configured to release the firing mechanism when the trigger is moved axially in a proximal direction relative to the housing, the trigger being configured to pass through the second opening of the outer casing;
    a boot covering a needle attached to the syringe to protect and maintain sterility of the needle;
    a first mechanical interlock configured to prevent actuation of the trigger prior to removal of the boot and to allow actuation or commencement of an actuation sequence following removal of the boot;
    a second mechanical interlock configured to detect pressure applied to the device by a user's skin following removal of the boot, and configured to prevent actuation of the trigger in absence of pressure and to allow actuation when sufficient pressure is detected; and
    a boot remover configured to remove the boot,
    wherein the boot remover provides said first mechanical interlock, the boot remover being disposed at the proximal end of the outer casing, and being further disposed, prior to removal, to hold the housing in a first position,
    wherein, in the first position, the housing is disposed proximally relative to the outer casing such that the proximal end of the housing projects through the first opening of the outer casing and the trigger is held within the outer casing, thereby restricting access to the trigger.

2. The automatic injection device according to claim 1, wherein the boot remover is formed integrally with the boot.

3. The automatic injection device according to claim 1, wherein the boot and boot remover are formed as separate discrete components, and configured such that the boot is locked into the boot remover upon insertion of the syringe into the housing.

4. The automatic injection device according to claim 1, wherein said first mechanical interlock comprises said boot remover, the boot remover being configured such that removal of the boot remover from the housing both removes the boot from the needle and facilitates access to the trigger.

5. The automatic injection device according to claim 1, wherein said second mechanical interlock comprises a biasing device acting between the outer casing and the housing, and configured such that when the boot remover is removed, the biasing device moves the housing in a distal direction relative to the outer casing to a second position, such that at least a part of the trigger protrudes from the distal opening of the outer casing, allowing access to the trigger.

6. The automatic injection device according to claim 5, wherein, following removal of the boot remover and boot, when the proximal end of the outer casing is placed against the user's skin, applying force to the trigger in a proximal direction causes the proximal end of the housing to be pressed against the skin, and causes the trigger to be displaced axially relative to the housing, activating the device.

* * * * *